US012303626B2

(12) United States Patent
Morita

(10) Patent No.: US 12,303,626 B2
(45) Date of Patent: May 20, 2025

(54) ATTACHING MEMBER

(71) Applicant: Nikkiso Company Limited, Tokyo (JP)

(72) Inventor: Masayuki Morita, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 957 days.

(21) Appl. No.: 17/347,852

(22) Filed: Jun. 15, 2021

(65) Prior Publication Data

US 2021/0308348 A1  Oct. 7, 2021

Related U.S. Application Data

(63) Continuation of application No. PCT/JP2019/035412, filed on Sep. 9, 2019.

(30) Foreign Application Priority Data

Dec. 27, 2018  (JP) .................................. 2018-246172

(51) Int. Cl.
*A61M 60/113* (2021.01)
*A61M 1/16* (2006.01)
(Continued)

(52) U.S. Cl.
CPC ........ *A61M 1/1645* (2014.02); *A61M 1/1654* (2013.01); *A61M 1/3403* (2014.02);
(Continued)

(58) Field of Classification Search
CPC .... A61M 1/14; A61M 1/1645; A61M 1/3403; A61M 1/3424; A61M 1/3621;
(Continued)

(56) References Cited

U.S. PATENT DOCUMENTS 5,427,509 A * 6/1995 Chapman ........ A61M 1/362261
604/153
5,928,177 A * 7/1999 Brugger .............. A61M 60/279
604/6.11

(Continued)

FOREIGN PATENT DOCUMENTS

EP   2682608 A1   1/2014
EP   1942964 B1   8/2015
(Continued)

OTHER PUBLICATIONS

Potentially related patent application filed herewith and published as WO2020/138380 A1.
(Continued)

*Primary Examiner* — Catharine L Anderson
*Assistant Examiner* — Jihad Dakkak
(74) *Attorney, Agent, or Firm* — Young Basile Hanlon & MacFarlane, P.C.

(57) ABSTRACT

An attaching member is provided that is capable of releasing a load occurring on a pump tube that is being attached to or detached from a peristaltic pump so that the work of attaching or detaching the pump tube to or from the peristaltic pump can be performed stably. An attaching member to be attached to a blood purification apparatus including peristaltic pumps holds pump tubes to be squeezed in a predetermined direction by the peristaltic pumps for liquid delivery. The attaching member includes a body attachable to a predetermined position of the blood purification apparatus, and holding portions attached to the body and that hold the pump tubes. The holding portions are displaceable relative to the body by rocking.

14 Claims, 26 Drawing Sheets

(51) Int. Cl.
*A61M 1/34* (2006.01)
*A61M 60/279* (2021.01)
*A61M 60/37* (2021.01)

(52) U.S. Cl.
CPC ........ *A61M 60/113* (2021.01); *A61M 60/279* (2021.01); *A61M 60/37* (2021.01); *A61M 2205/15* (2013.01); *A61M 2209/082* (2013.01)

(58) Field of Classification Search
CPC .............. A61M 1/367; A61M 2205/15; A61M 2209/082; A61M 5/14232; A61M 60/104; A61M 60/109; A61M 60/113; A61M 60/279; A61M 60/37; A61M 60/845; A61M 60/847; F04B 3/12; F04B 43/08; F04B 43/086; F04B 53/22; F04B 43/082; F04B 43/1284; F04B 43/1292
See application file for complete search history.

(56) References Cited

U.S. PATENT DOCUMENTS

| | | | |
|---|---|---|---|
| 6,284,141 B1* | 9/2001 | Shaldon | A61M 1/16 210/143 |
| 2003/0125674 A1* | 7/2003 | Cise | A61M 39/24 604/247 |
| 2003/0216714 A1* | 11/2003 | Gill | A61M 5/14232 604/890.1 |
| 2004/0162513 A1* | 8/2004 | Neri | A61M 1/3621 604/6.09 |
| 2005/0069436 A1 | 3/2005 | Shibasaki | |
| 2005/0089994 A1* | 4/2005 | Neftel | A61M 1/14 435/287.1 |
| 2008/0213113 A1* | 9/2008 | Lawrence | F16L 3/1041 417/477.2 |
| 2014/0219829 A1* | 8/2014 | Matsuo | A61M 60/857 417/63 |
| 2015/0021244 A1* | 1/2015 | Furuhashi | A61M 1/3458 210/85 |

FOREIGN PATENT DOCUMENTS

| | | |
|---|---|---|
| JP | 860-148069 U | 10/1985 |
| JP | 2005-074234 A | 3/2005 |
| JP | 2006-212050 A | 8/2006 |
| JP | 2008-000425 A | 1/2008 |
| JP | 2010-190062 A | 9/2010 |
| JP | 2015-073847 A | 4/2015 |
| JP | 2015-202248 A | 11/2015 |
| JP | 2017-140521 A | 8/2017 |
| JP | 2017-164285 A | 9/2017 |
| WO | 1995/017603 A1 | 6/1995 |
| WO | 1996/040322 A2 | 12/1996 |
| WO | 2013/090579 A1 | 6/2013 |
| WO | 2013/098028 A1 | 7/2013 |
| WO | 2018/225027 A1 | 12/2018 |

OTHER PUBLICATIONS

Potentially related patent application filed herewith and published as WO2020/138381 A1.
Potentially related patent application that will be filed with the USPTO, and is published as WO2020/138382 A1.
Potentially related patent application that will be filed with the USPTO, and is published as WO2020/138383 A1.
Potentially related patent application that will be filed with the USPTO, and is published as WO2020/138384 A1.
European Search Report for Application No. 19904482.7, dated Jul. 21, 2022, 7 pgs.

* cited by examiner

[Fig. 1]
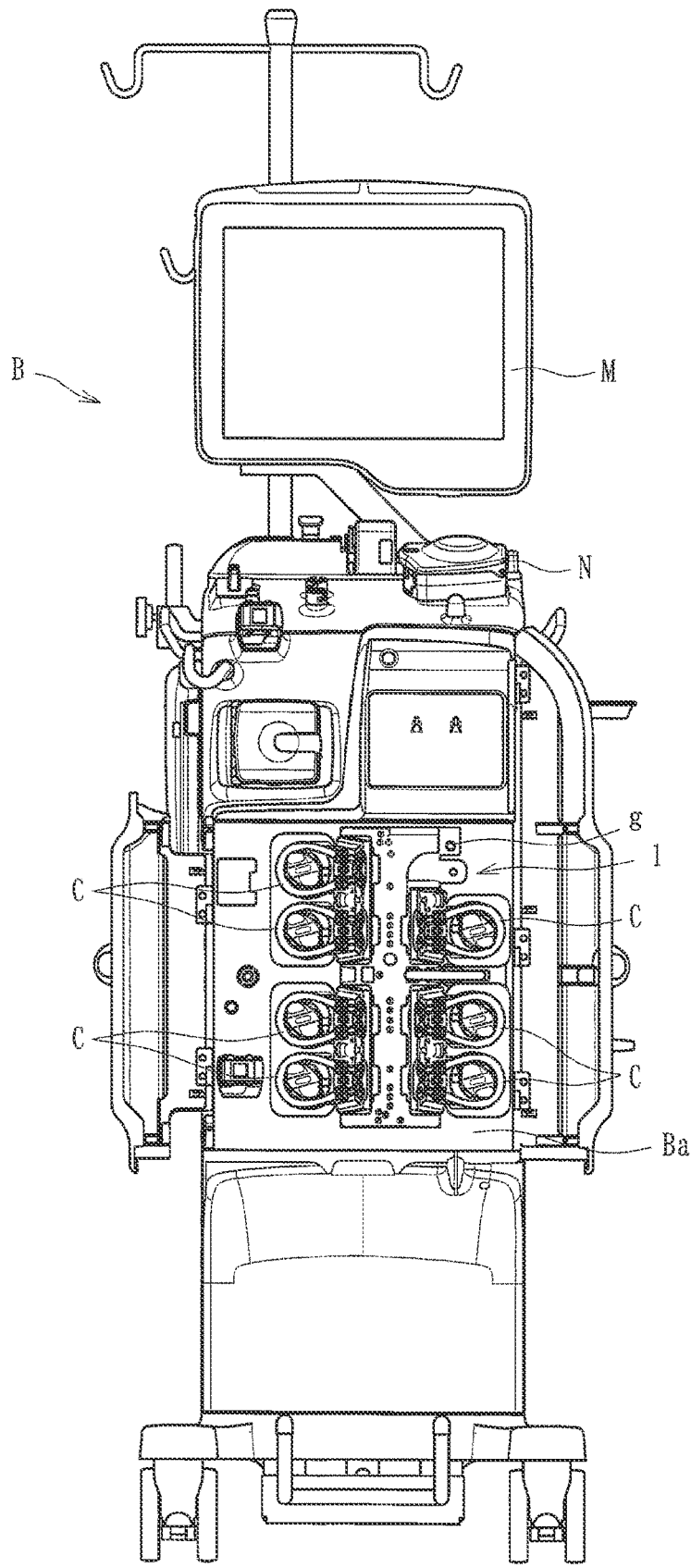

[Fig. 2]
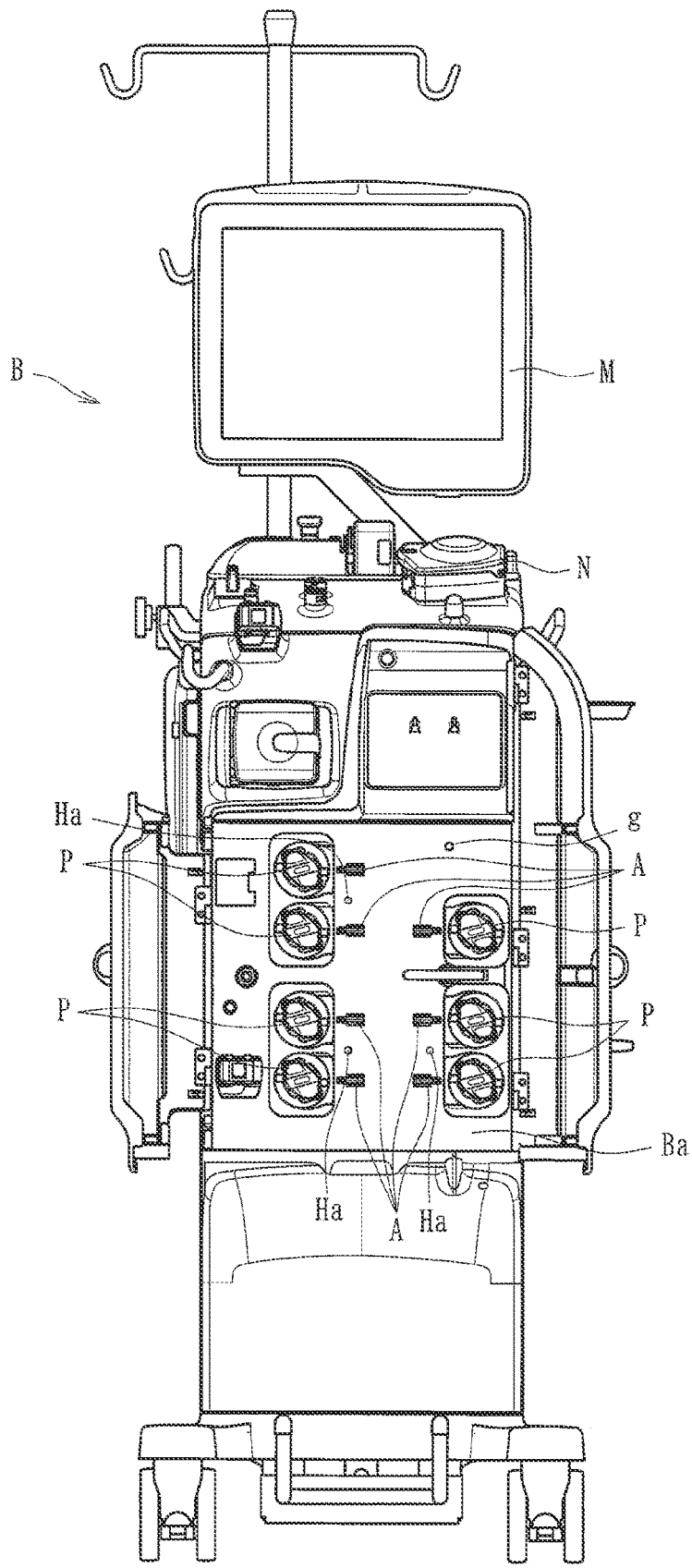

[ Fig. 3 ]
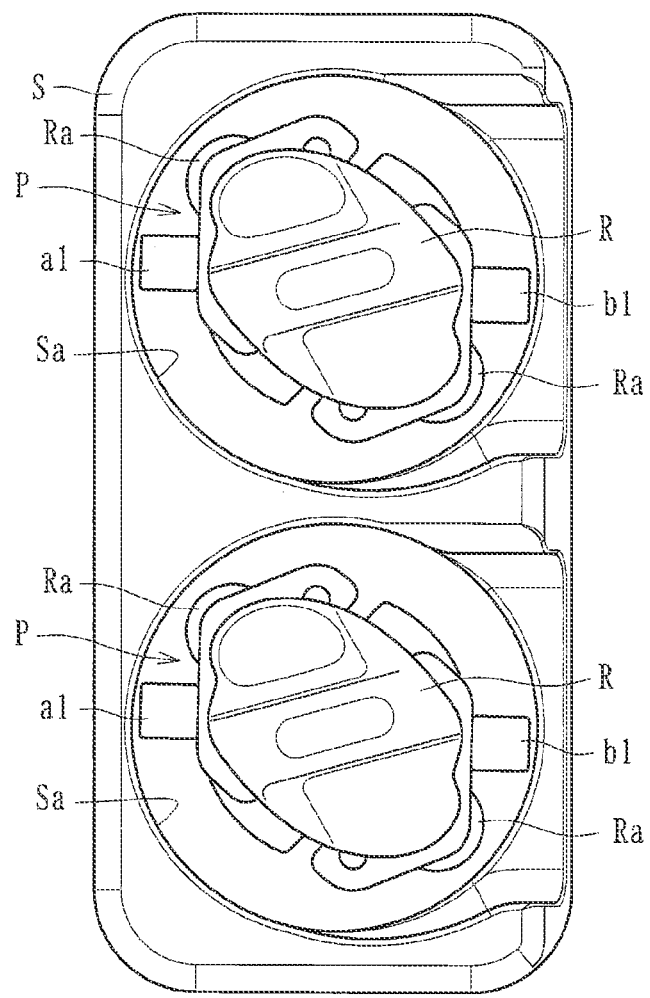

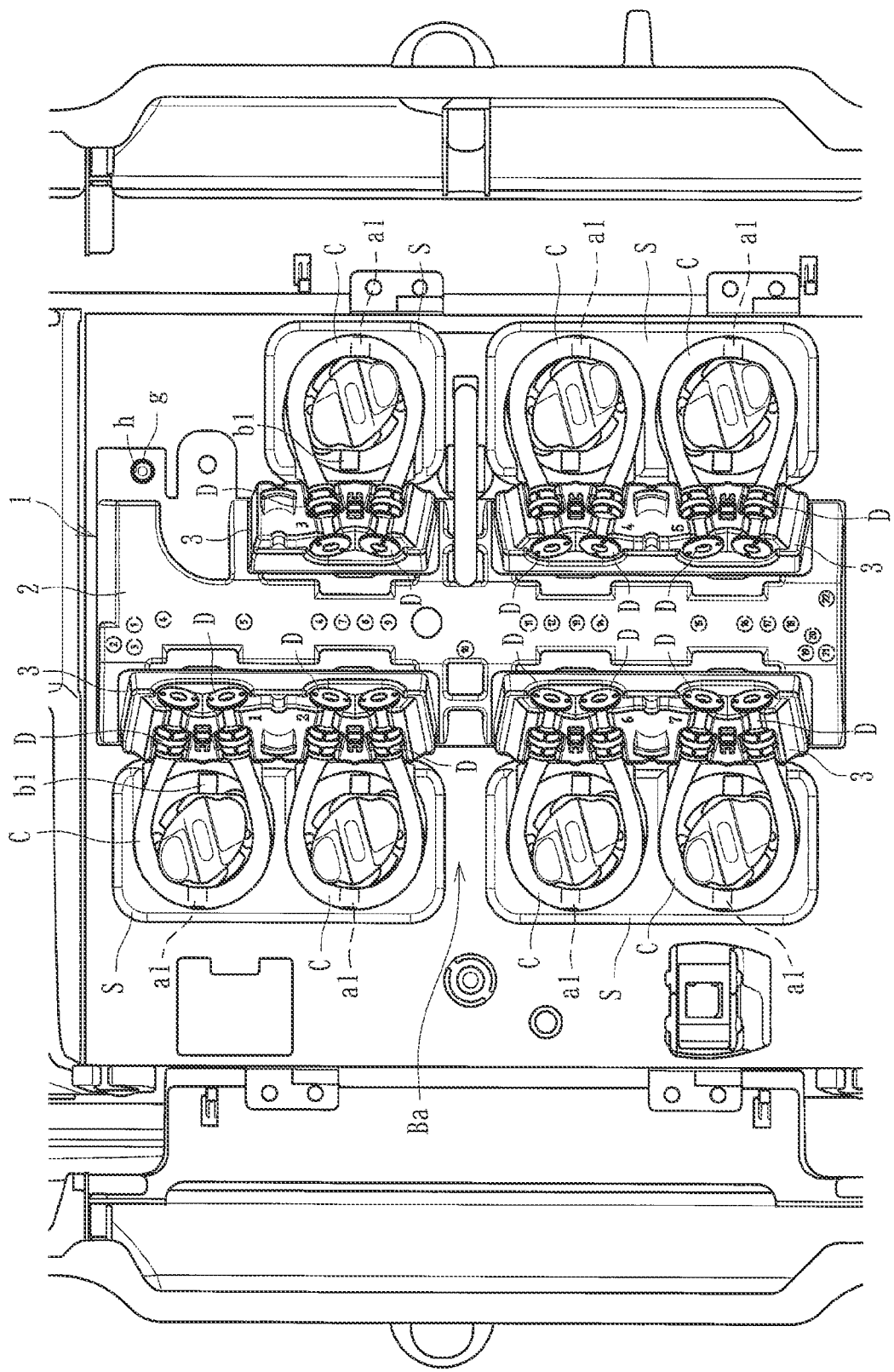
[Fig. 4]

[Fig. 5]
(a)
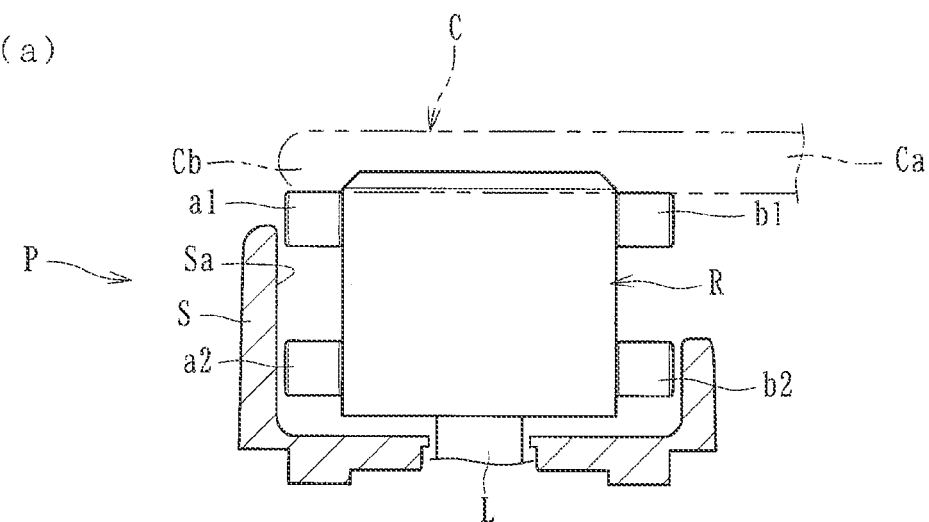
(b)
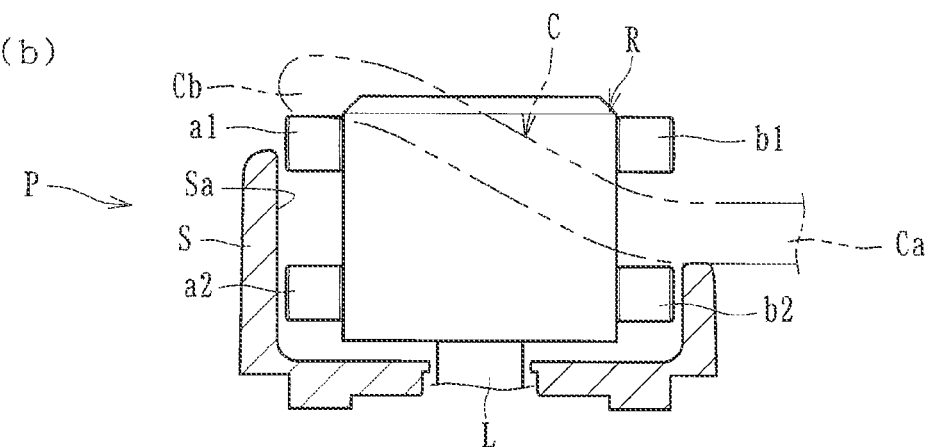
(c)
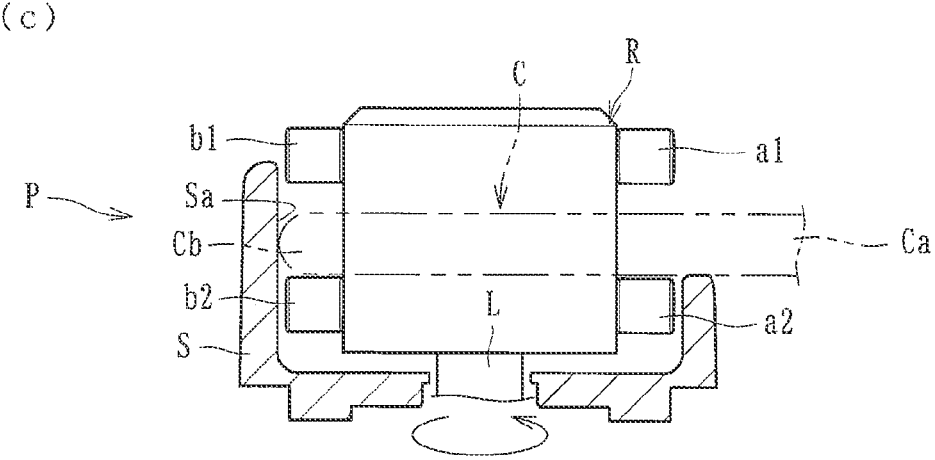

[Fig. 6]
(a)
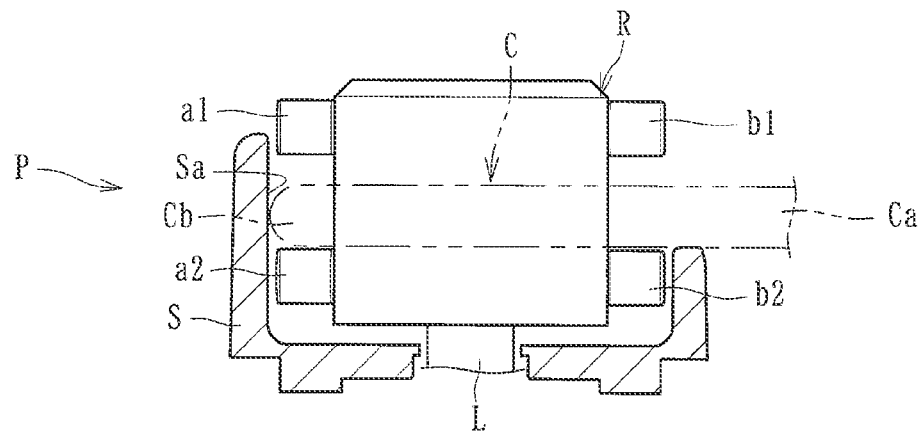
(b)
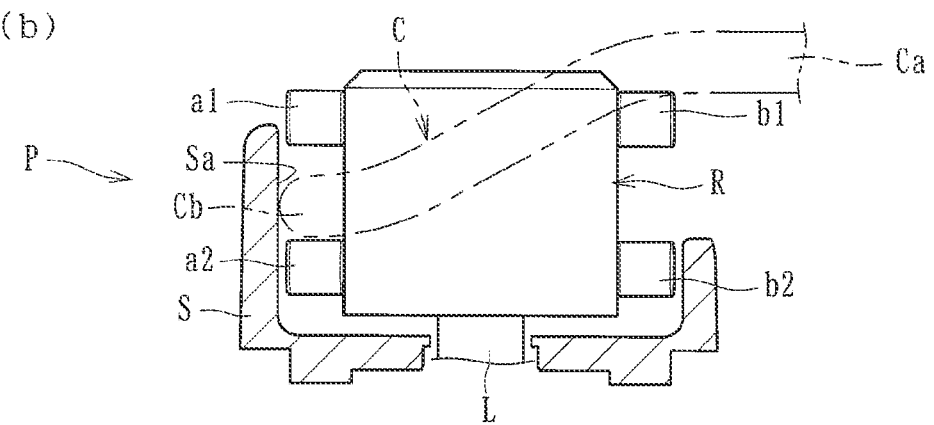
(c)
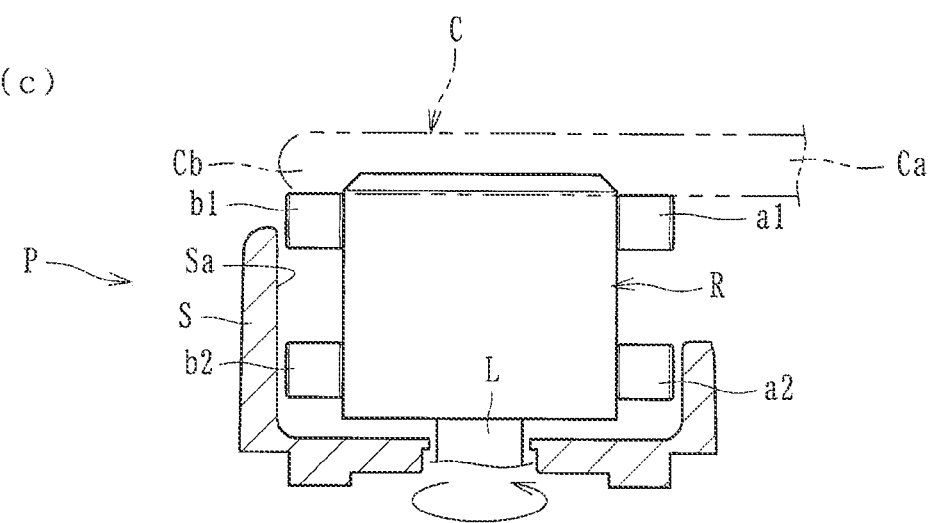

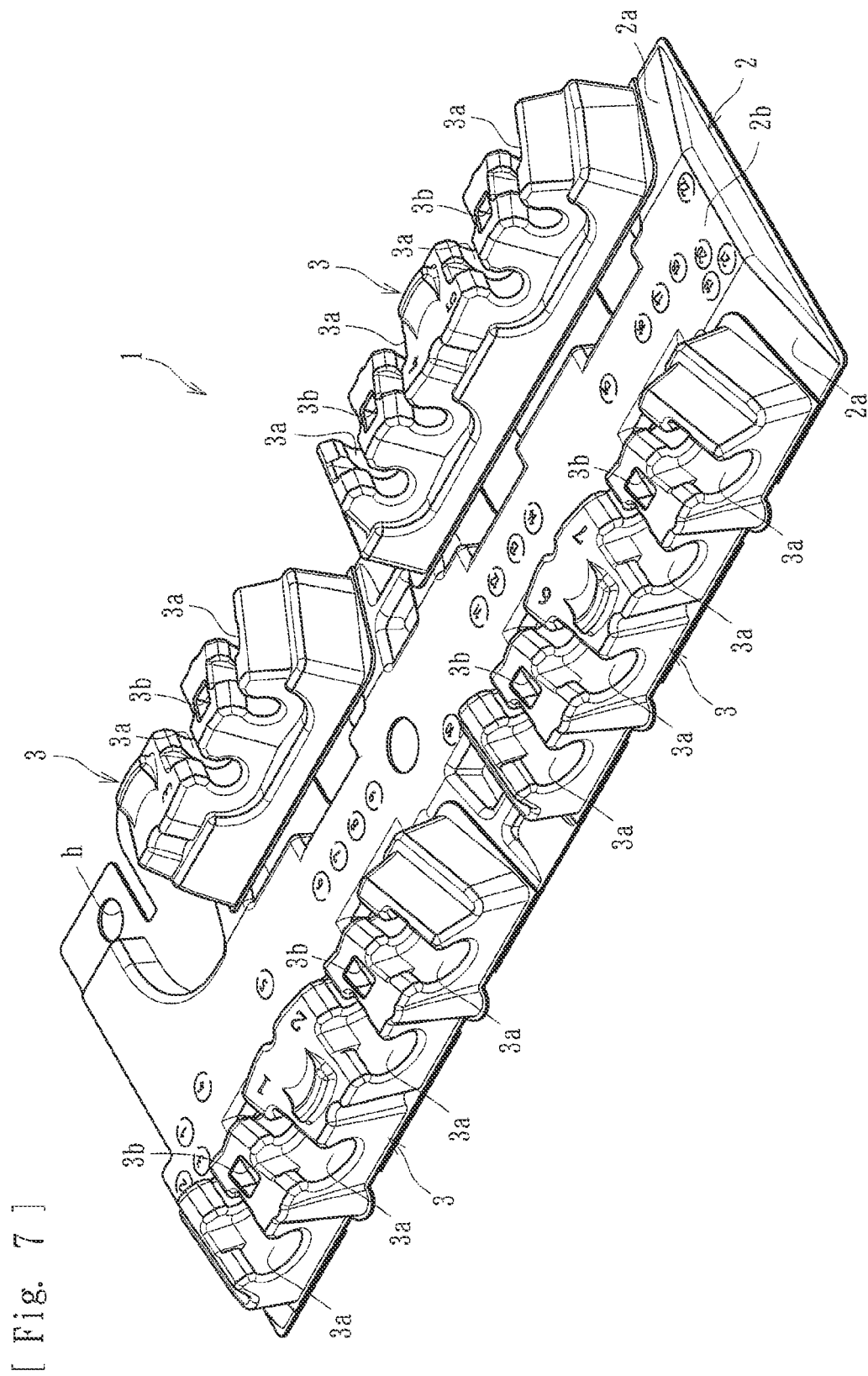
[Fig. 7]

[Fig. 8]
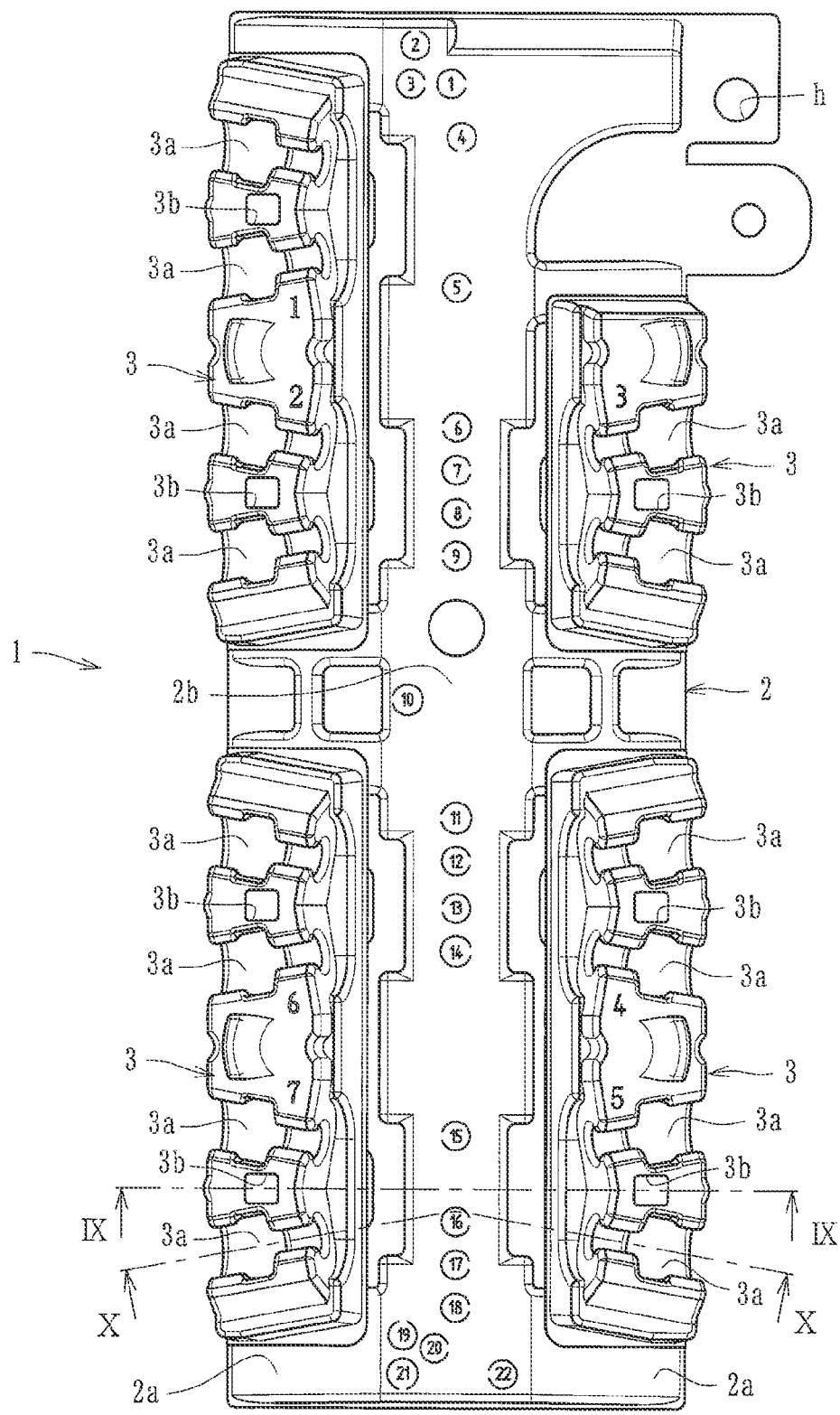

[Fig. 9]
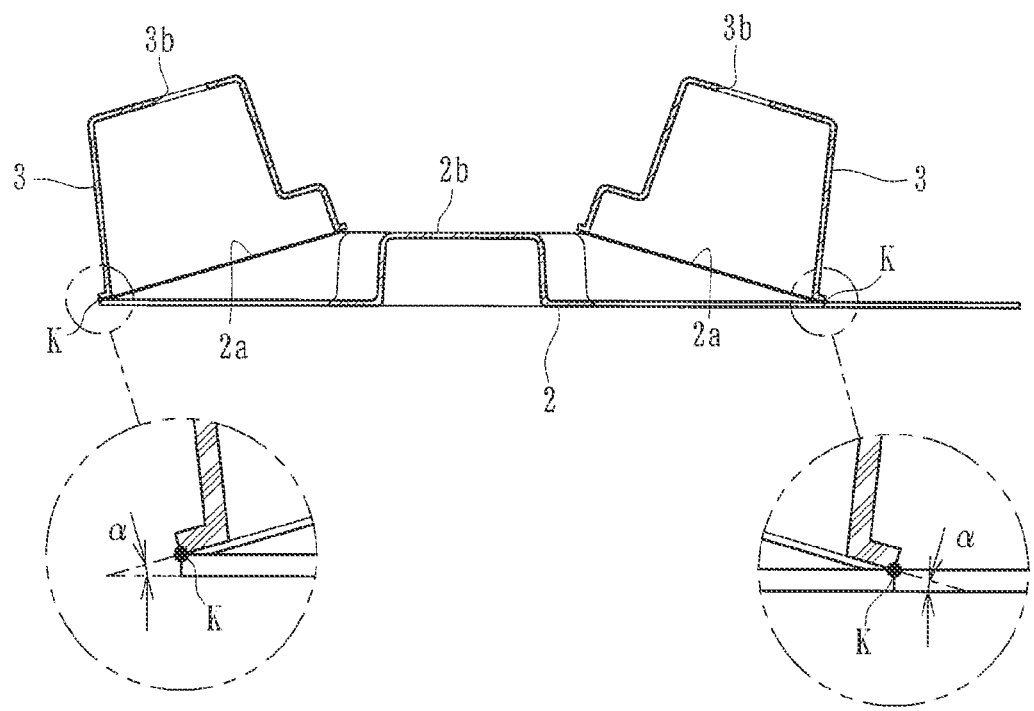
[Fig. 10]
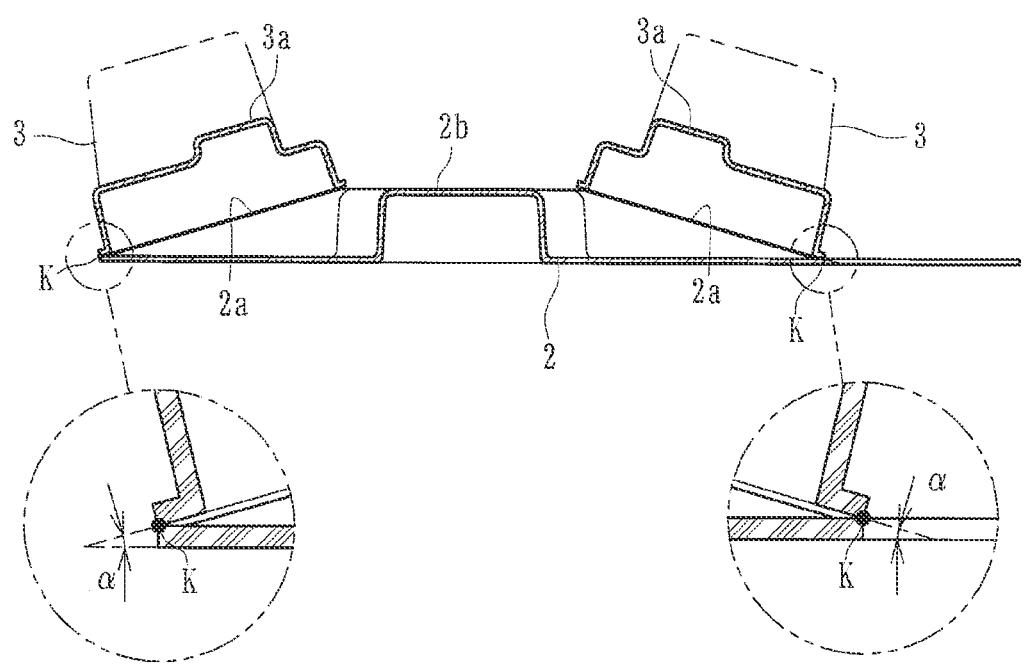

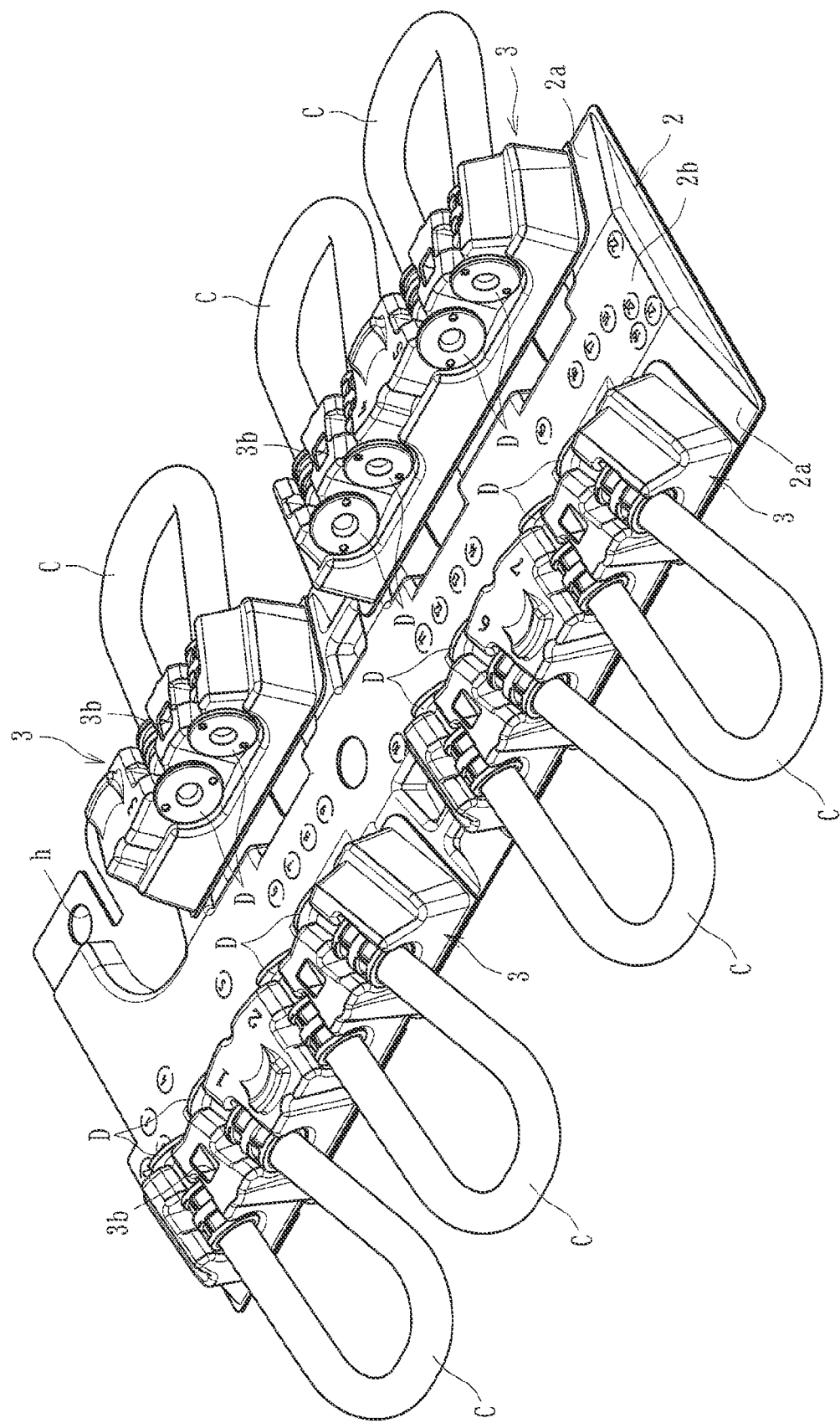
[Fig. 11]

[Fig. 12]
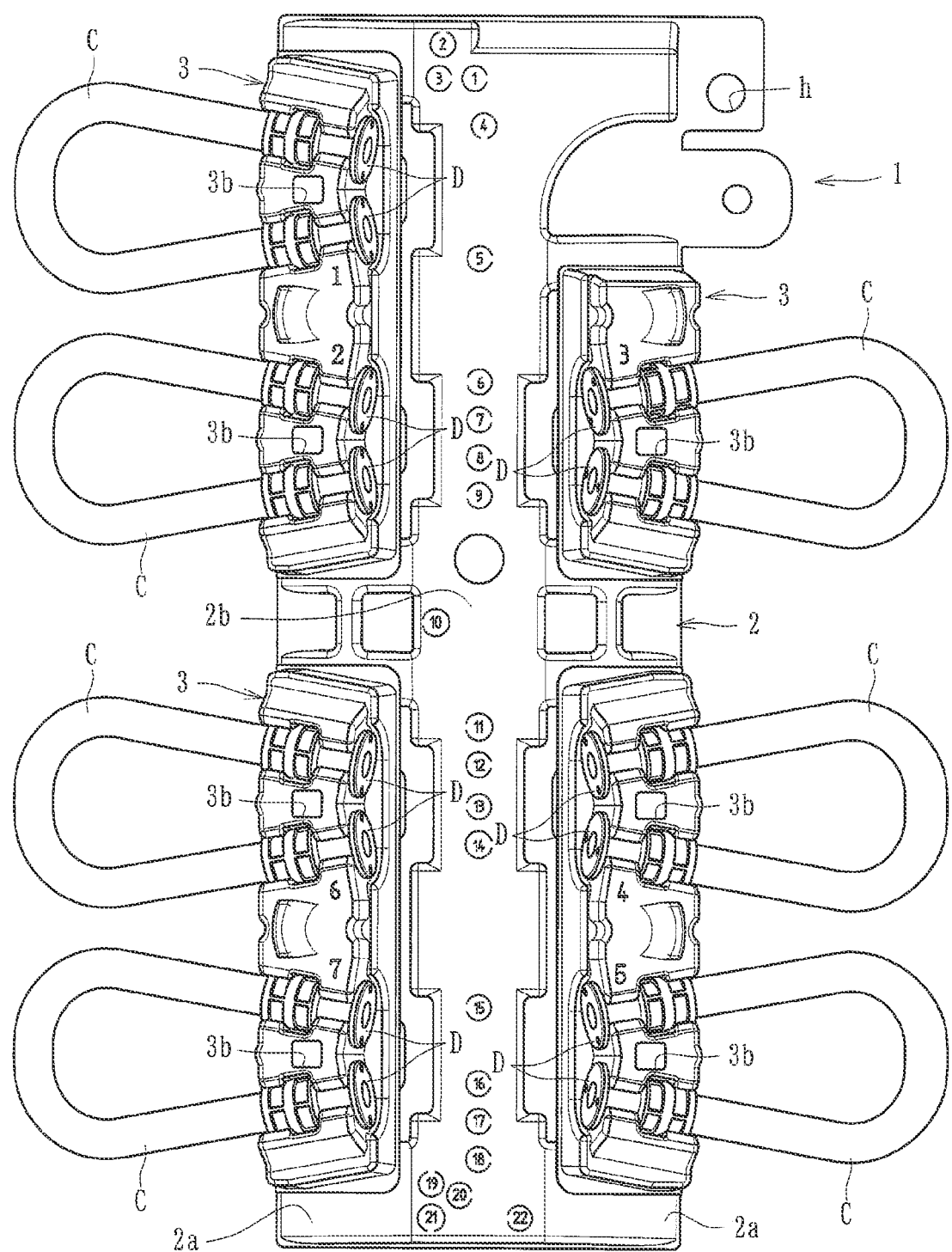

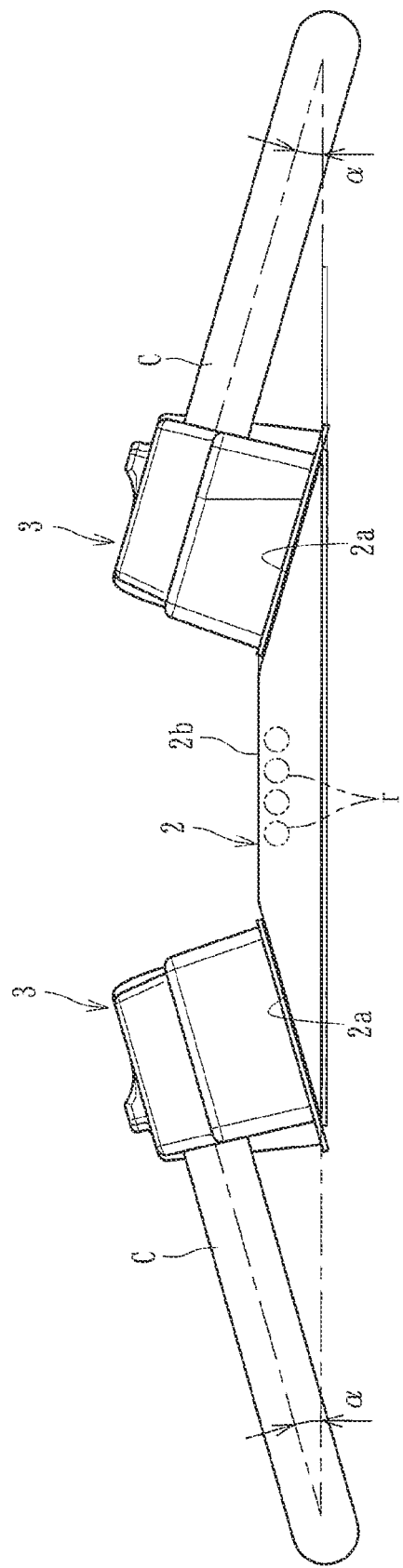
[Fig. 13]

[Fig. 14]
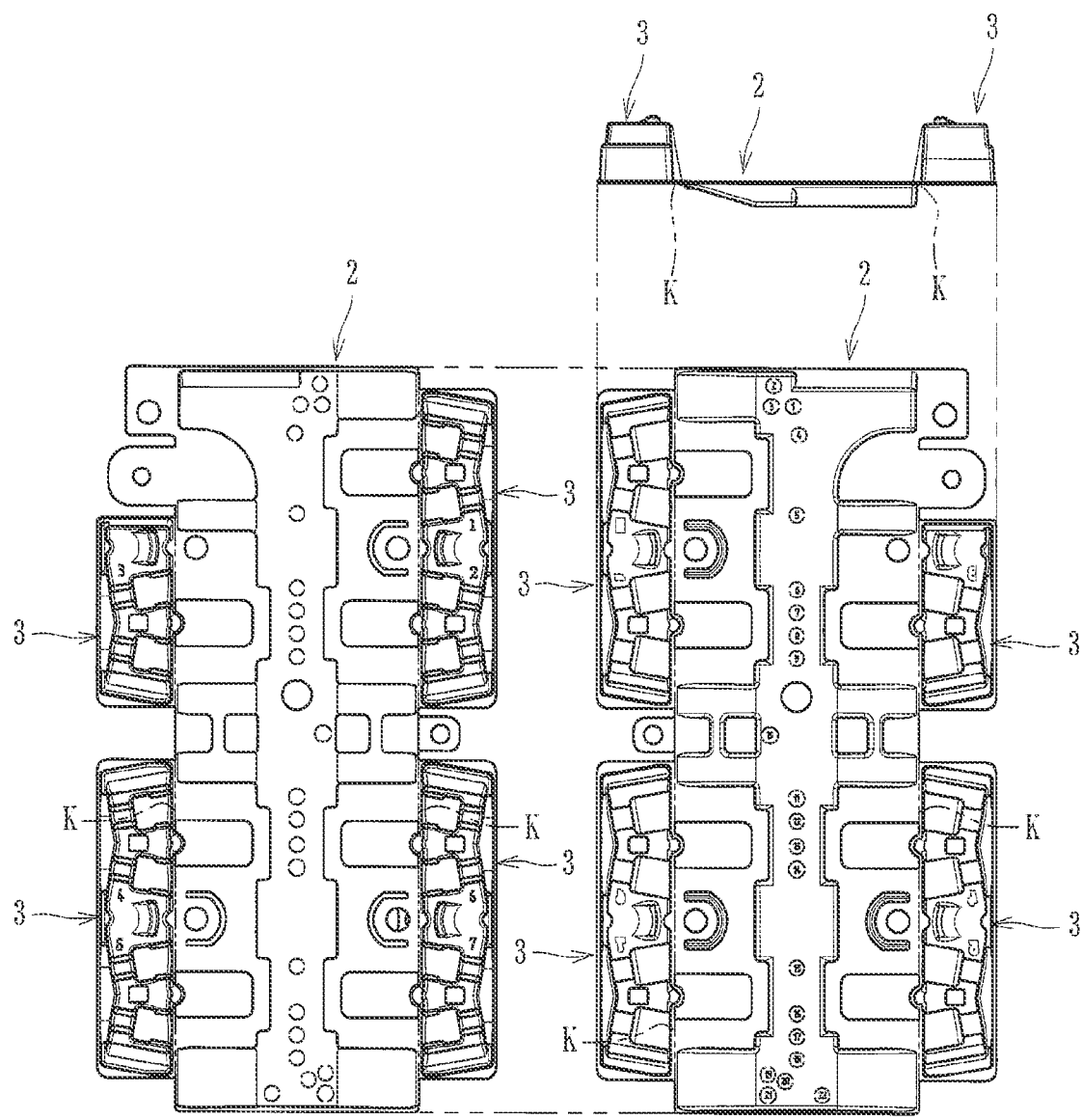

[Fig. 15]
(a)
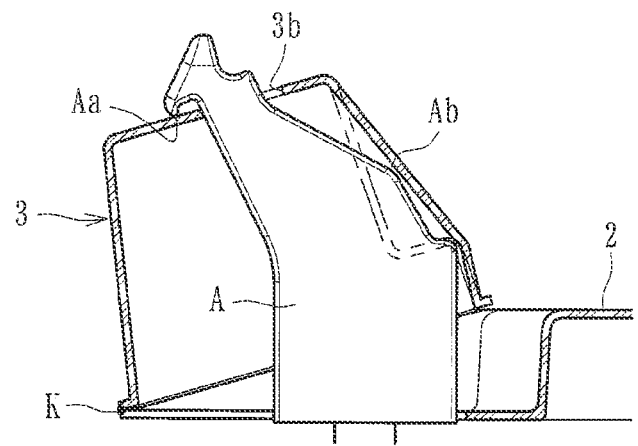
(b)
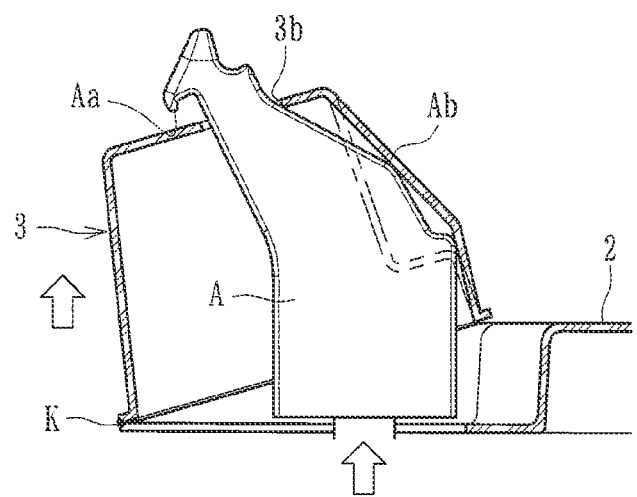
[Fig. 16]
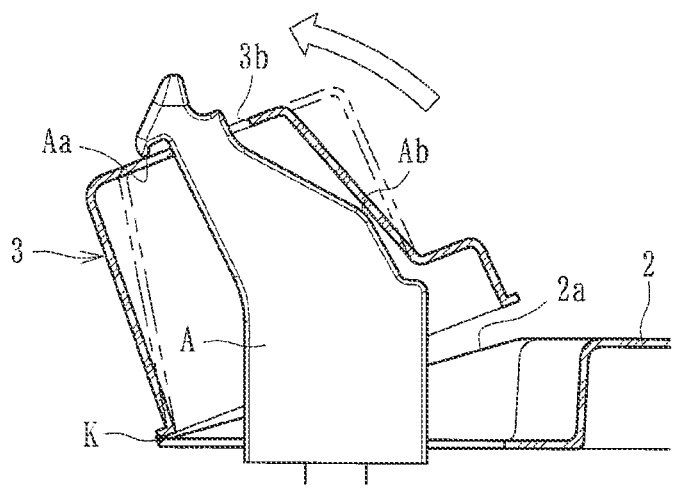

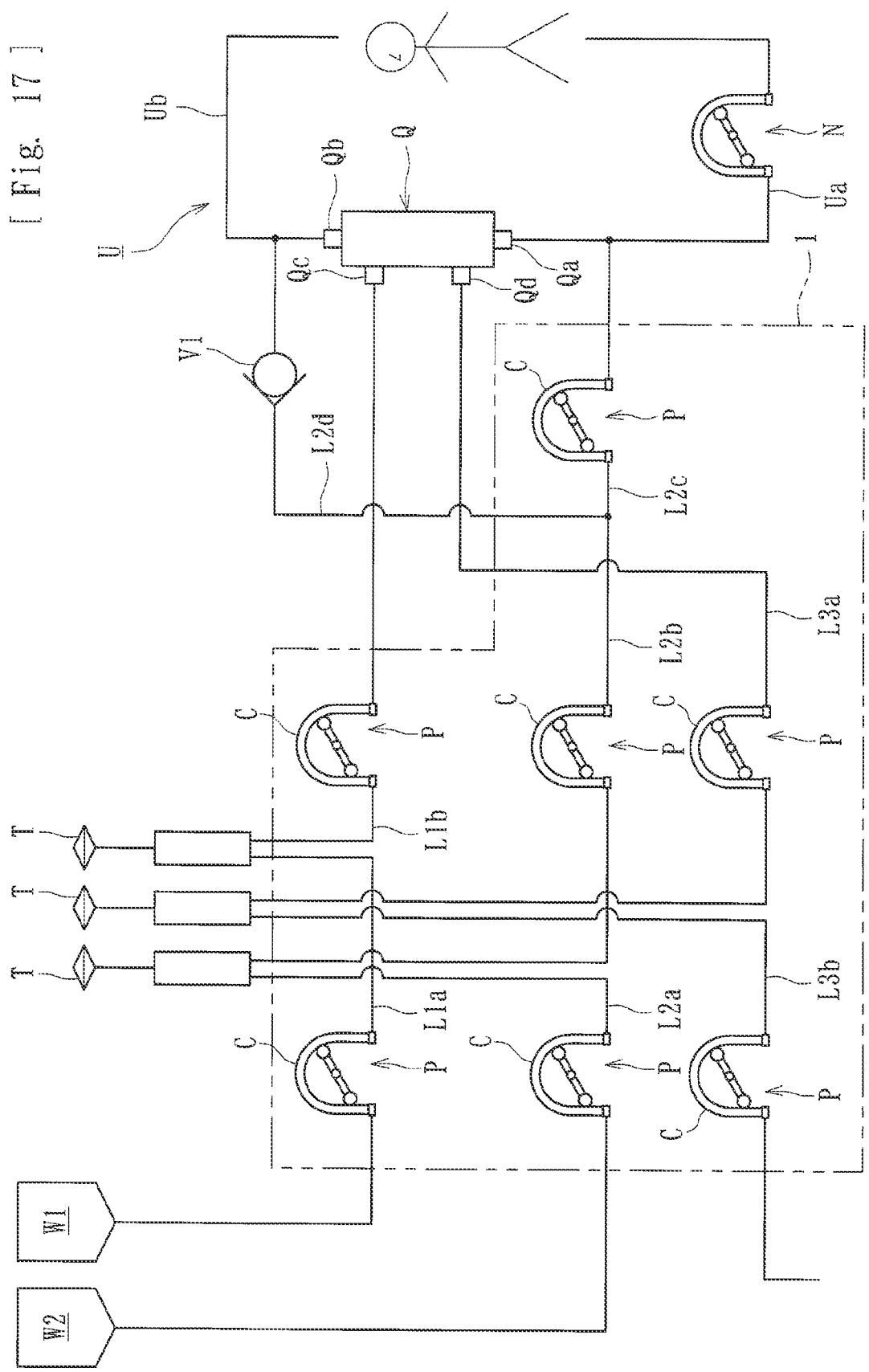
[Fig. 17]

[Fig. 18]
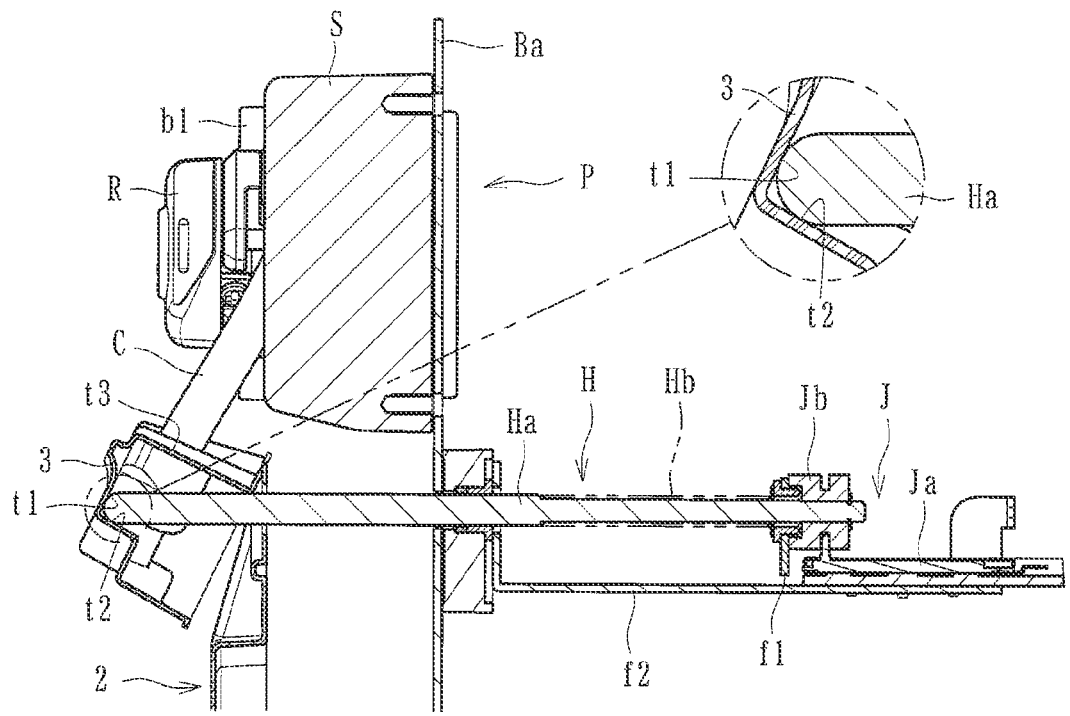
[Fig. 19]
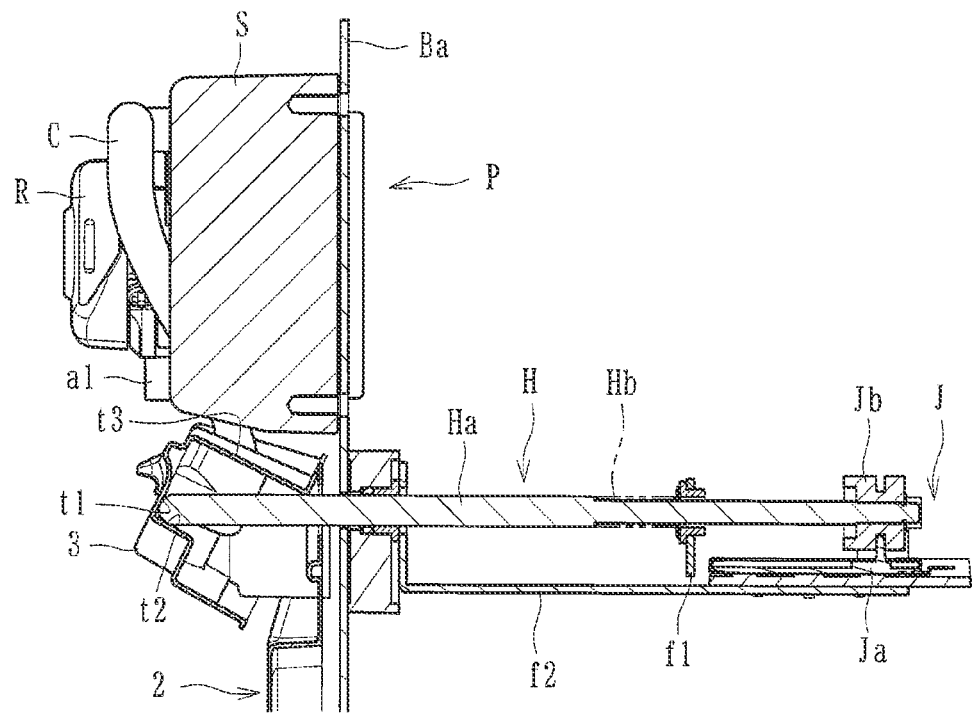

[Fig. 20]
(a)
(b)
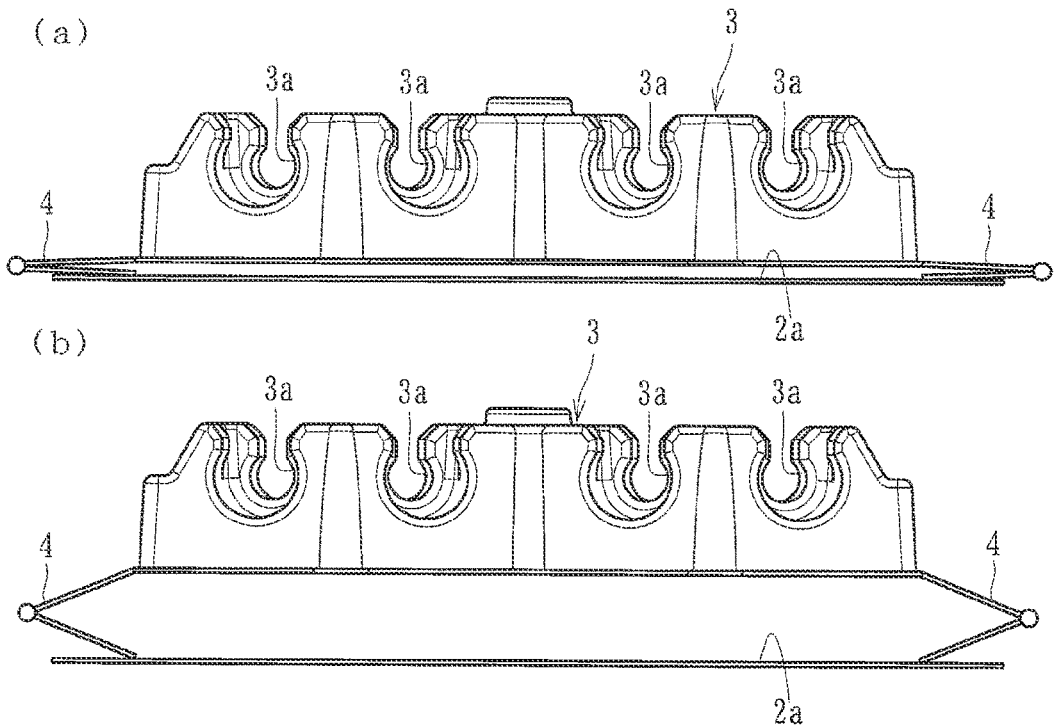
[Fig. 21]
(a)
(b)
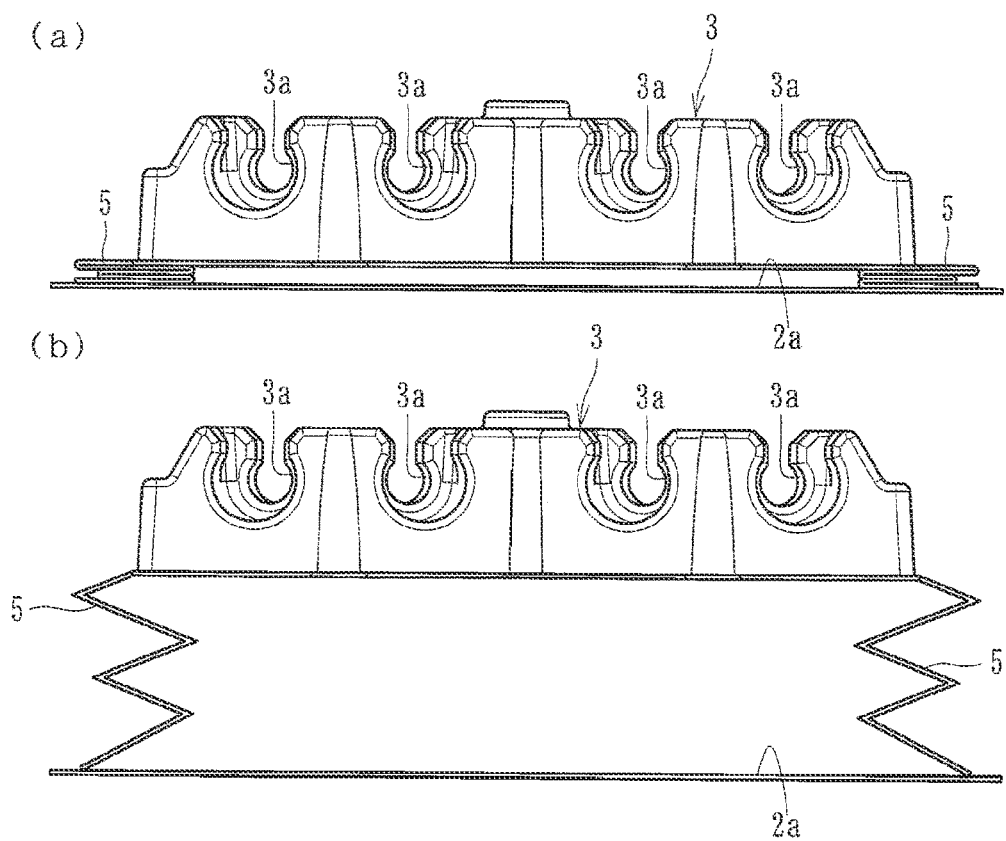

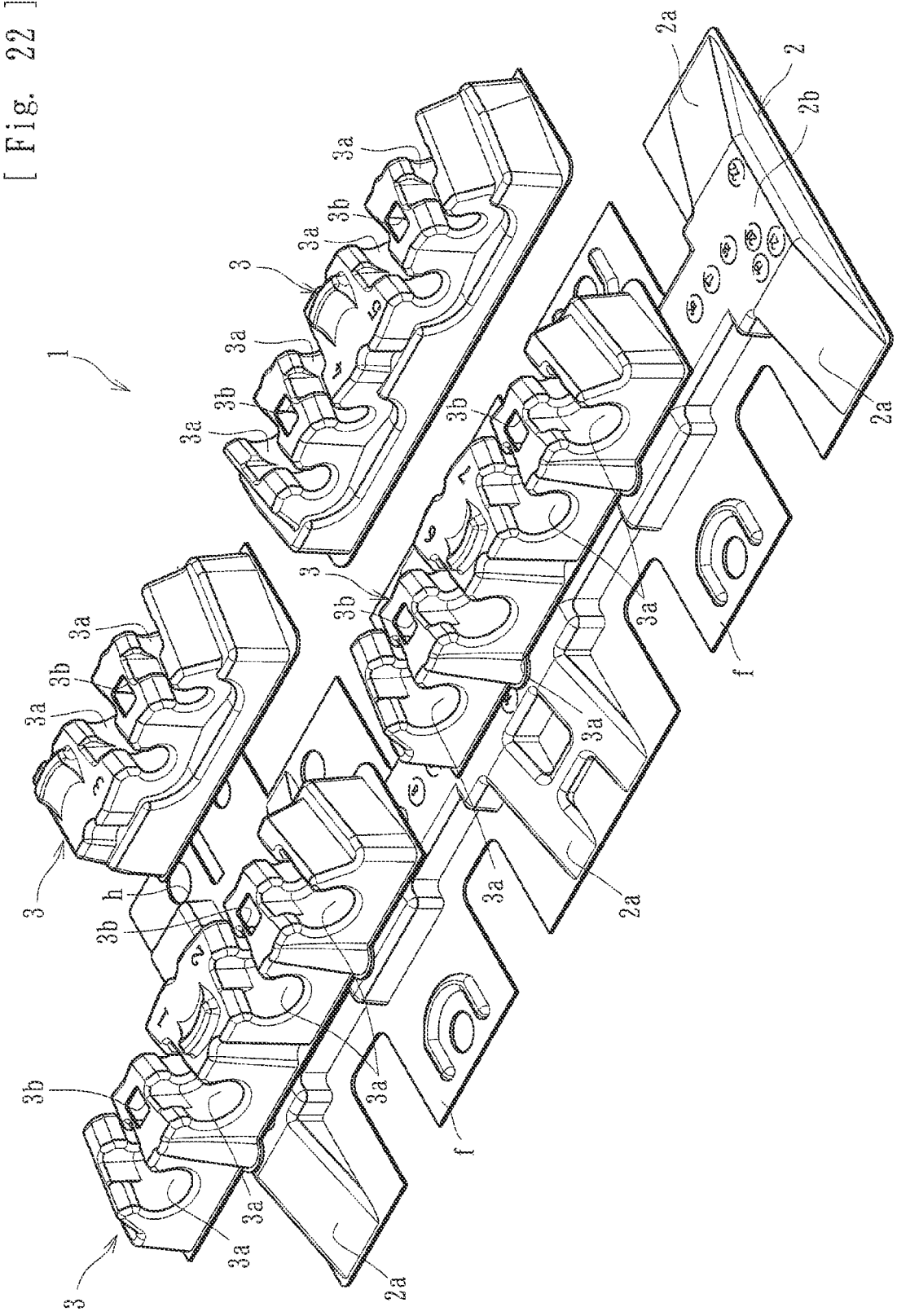
[Fig. 22]

[Fig. 23]
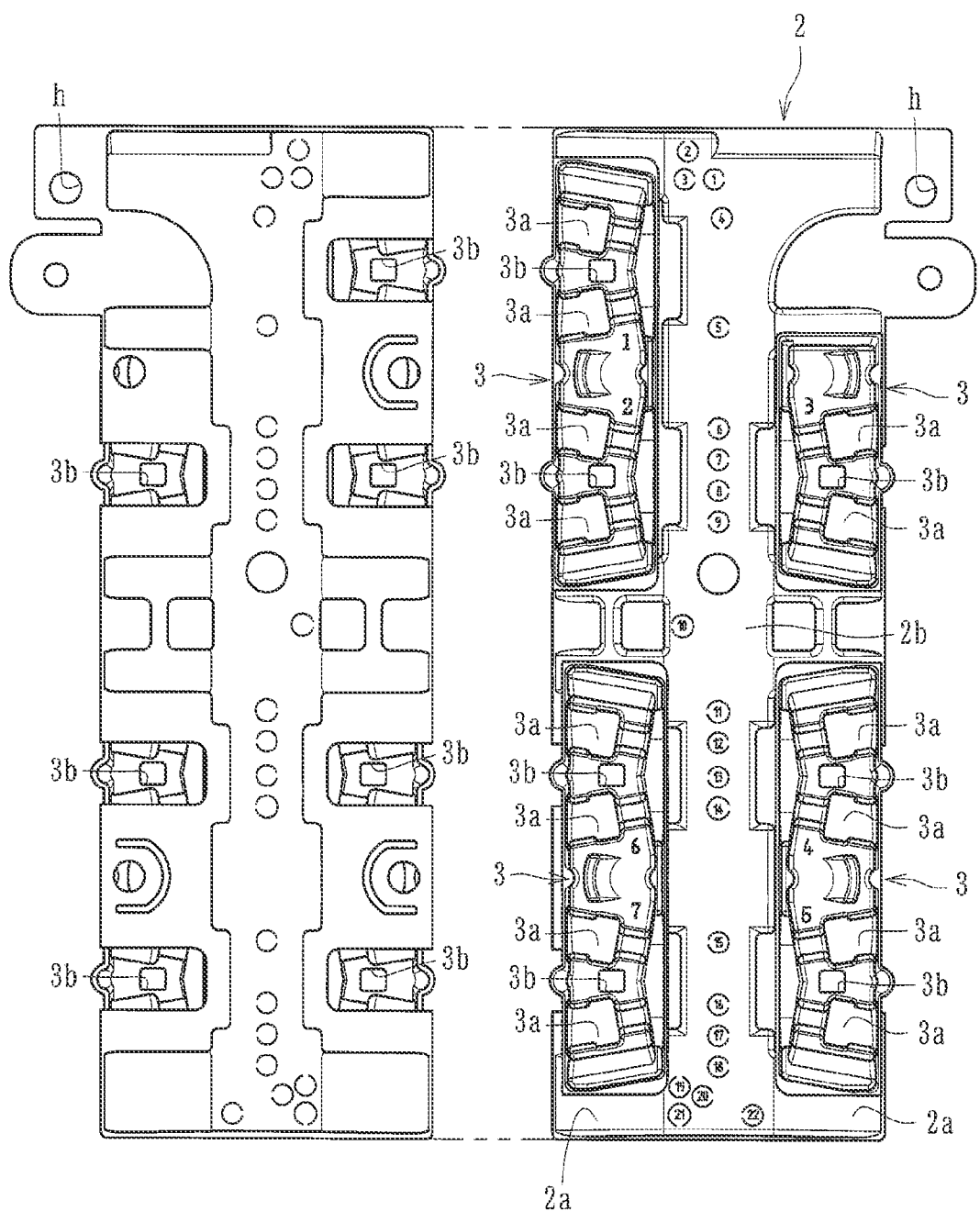

[Fig. 24]
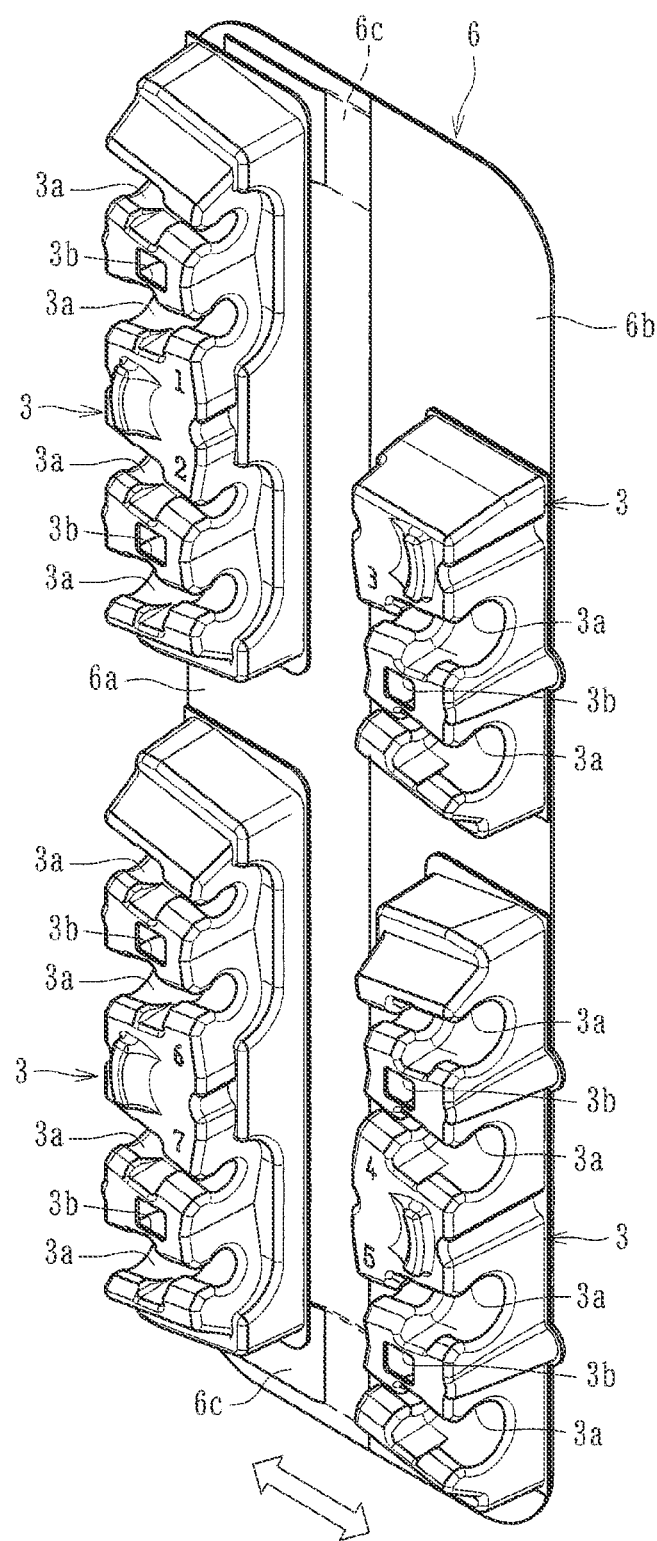

[Fig. 25]
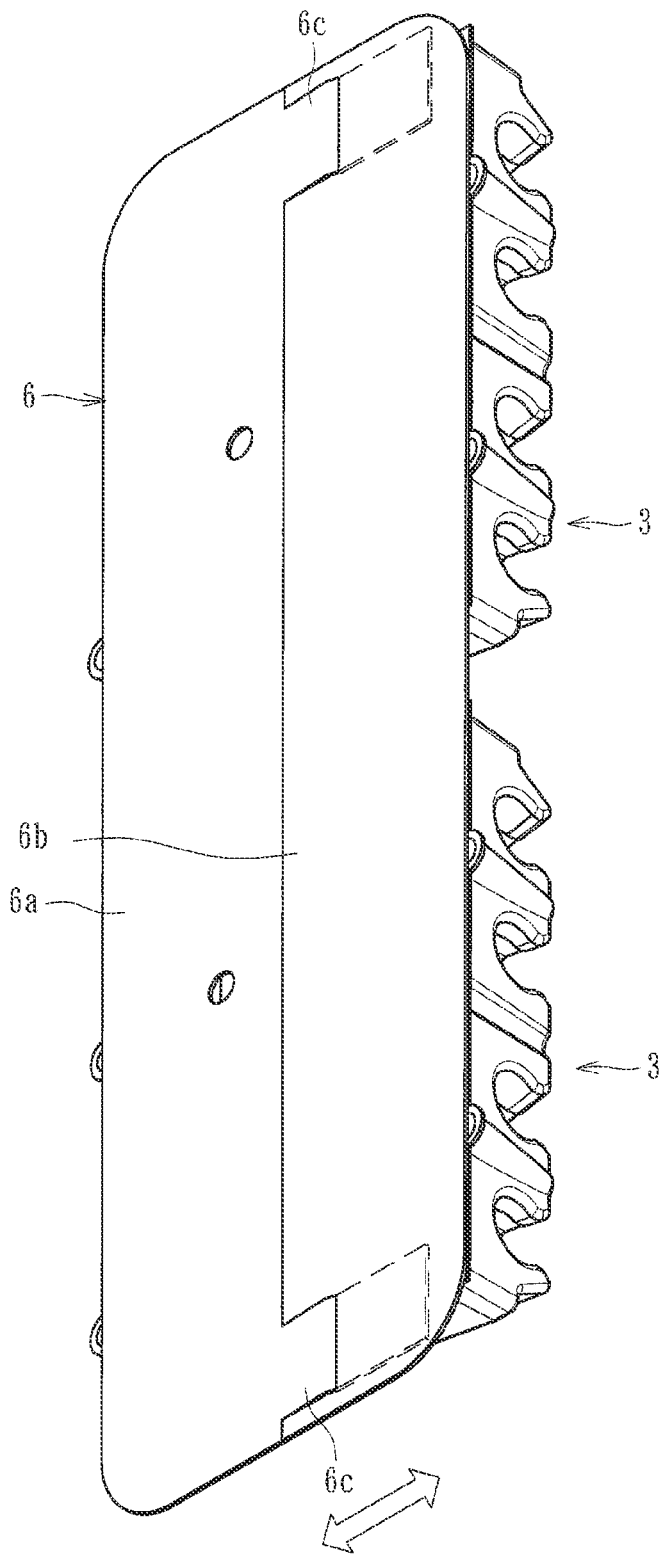

[Fig. 26]
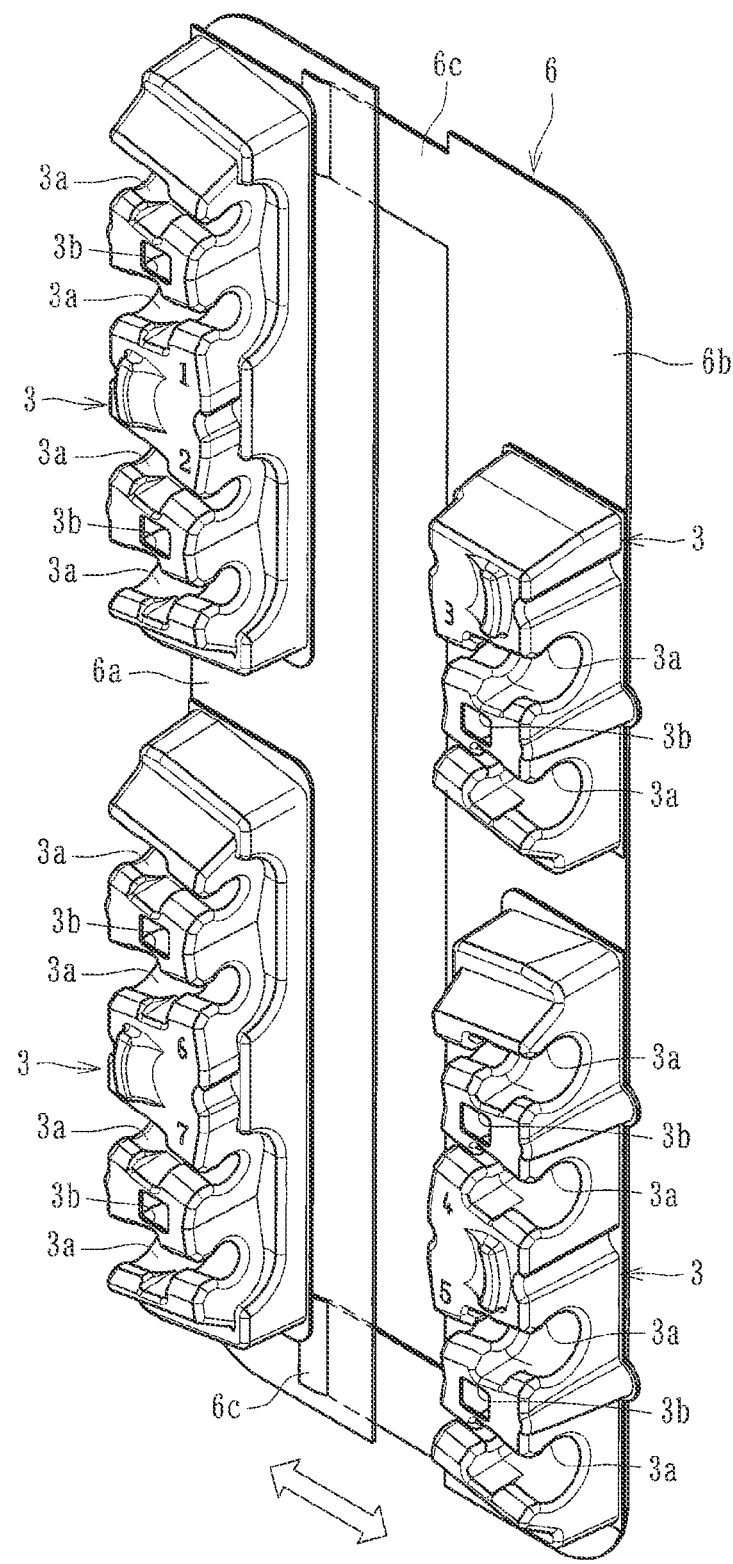

[Fig. 27]
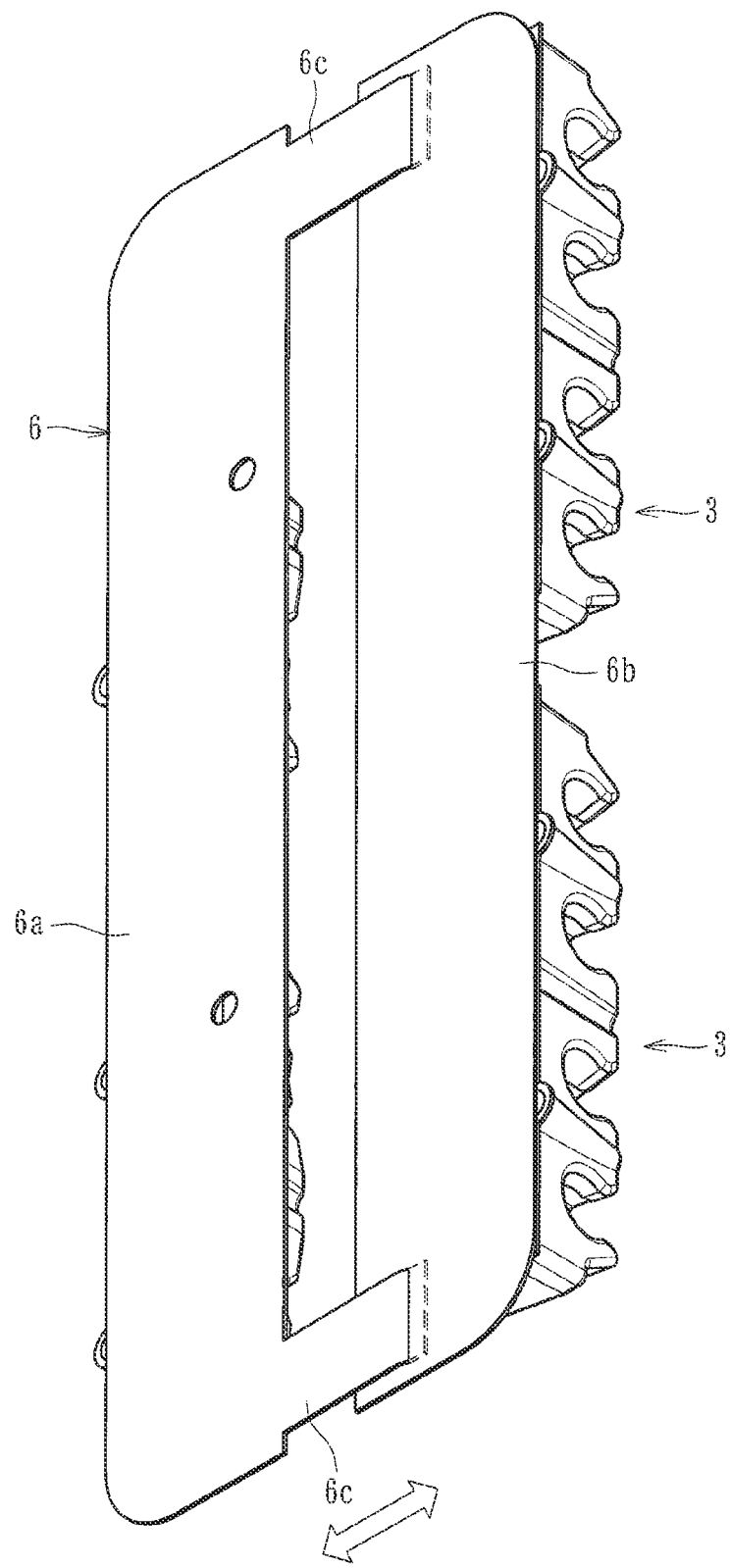

[Fig. 28]
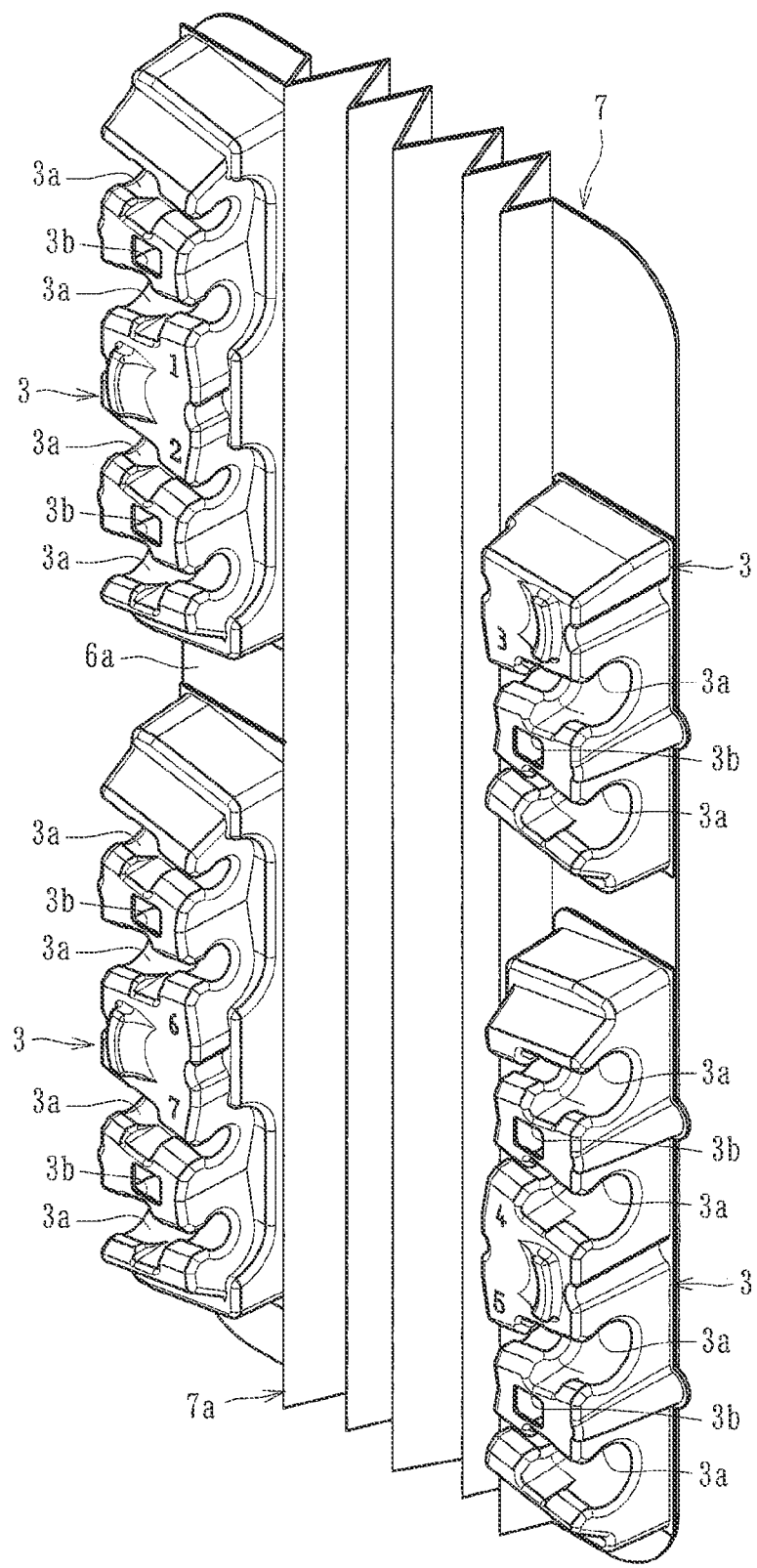

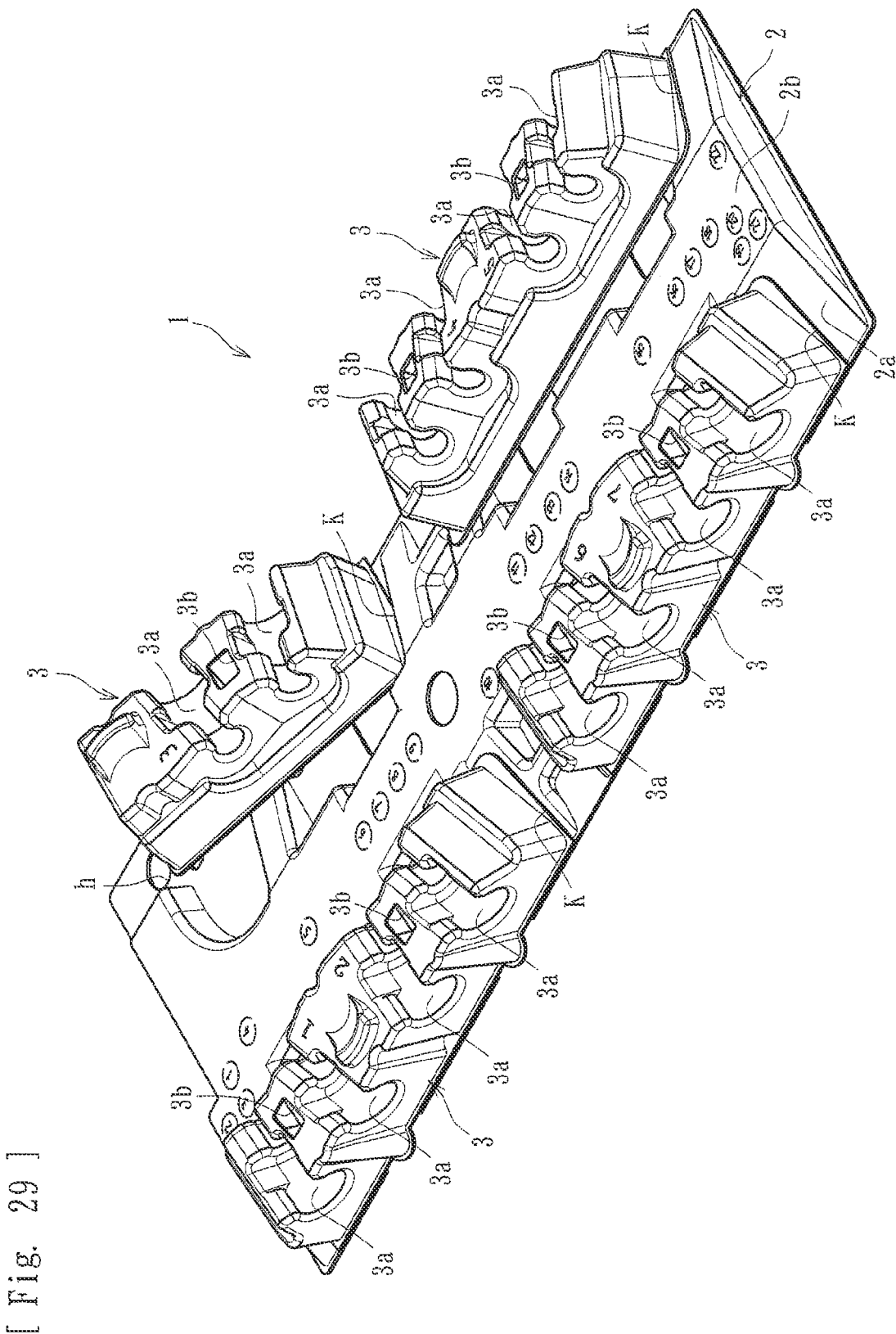
[Fig. 29]

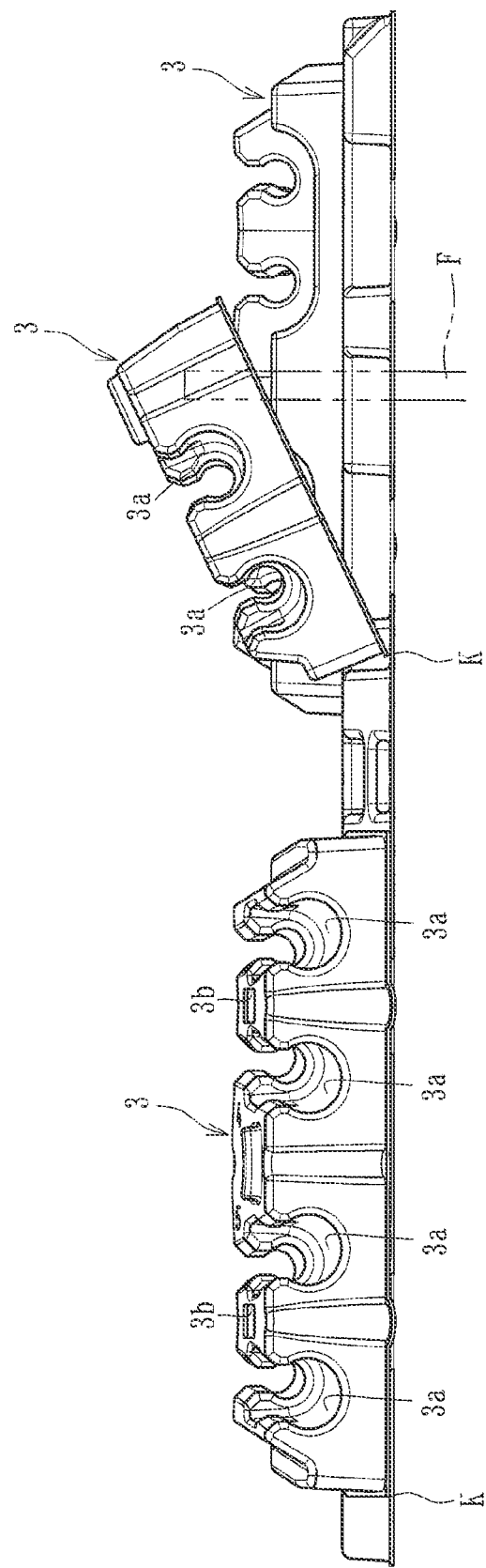
[Fig. 30]

ATTACHING MEMBER

CROSS-REFERENCE TO RELATED APPLICATION(S)

This application is a continuation of International Application No. PCT/JP2019/035412, filed on Sep. 9, 2019, which claims priority to Japanese Application No. 2018-246172, filed on Dec. 27, 2018, the entire disclosures of which are hereby incorporated by reference.

FIELD

The present teachings relate to an attaching member to be attached to a blood purification apparatus including a peristaltic pump, the attaching member holding a pump tube to be squeezed in a predetermined direction by the peristaltic pump for liquid delivery.

BACKGROUND

In general, a blood purification apparatus for giving dialysis treatment is provided with an arterial blood circuit and a venous blood circuit that form a blood circuit for causing blood of a patient to extracorporeally circulate, a blood purification device for purifying the blood extracorporeally circulating through the blood circuit, and various treatment devices, such as a blood pump, for performing blood purification treatment with the blood circuit and the blood purification device. After the patient is punctured with an arterial puncture needle and a venous puncture needle, the blood pump is activated. Thus, blood of the patient flows through the arterial blood circuit and the venous blood circuit. In such a flowing process, the blood is purified by the blood purification device.

Some of blood purification apparatuses according to existing proposals each include a plurality of peristaltic pumps for delivering liquids such as substitution fluid and drain liquid. The peristaltic pumps are provided with pump tubes, respectively, so that different liquids can be delivered. Hitherto, for example, an attaching member has been disclosed by PTL 1 that includes a plurality of pump tubes attachable to respective peristaltic pumps included in a blood purification apparatus. The attaching member is to be attached to a predetermined position of the blood purification apparatus.

PTL 1: Japanese Unexamined Patent Application Publication No. 2015-73847, the teachings of which are expressly incorporated by reference herein.

SUMMARY

In the above known attaching member, however, when the pump tubes are attached to or detached from the peristaltic pumps, the pump tubes may interfere with and be nipped between elements, such as guide pins and rotors, of the peristaltic pumps and may be subjected to a certain load. If the pump tubes are nipped and are subjected to a load, the work of attaching or detaching the pump tubes to or from the peristaltic pumps cannot be performed stably.

The present teachings have been conceived in view of the above circumstances and provides an attaching member capable of releasing a load occurring on a pump tube that is being attached to or detached from a peristaltic pump so that the work of attaching or detaching the pump tube to or from the peristaltic pump can be performed stably.

Variation 1 may include an attaching member to be attached to a blood purification apparatus including a peristaltic pump, the attaching member holding a pump tube to be squeezed in a predetermined direction by the peristaltic pump for liquid delivery. The attaching member includes a body attachable to a predetermined position of the blood purification apparatus, and a holding portion attached to the body and that holds the pump tube. The holding portion is displaceable relative to the body.

Variation 2 may comprise the attaching member according to variation 1, the holding portion includes an anchoring part at which the holding portion is anchorable by an anchor member included in the blood purification apparatus, and the pump tube is attachable to the peristaltic pump when the holding portion is anchored by the anchor member at the anchoring part.

Variation 3 may comprise the attaching member according to variation 1 or 2, the holding portion includes an anchoring part at which the holding portion is anchorable by an anchor member included in the blood purification apparatus, and the pump tube is detachable from the peristaltic pump by moving the anchor member when the anchor member is anchored to the holding portion at the anchoring part.

Variation 4 may comprise the attaching member according to any of variations 1 to 3, the holding portion is displaceable by rocking relative to the body.

Variation 5 may comprise the attaching member according to variation 4, the holding portion is continuous with and folded with respect to the body and is rockable about the folded area.

Variation 6 may comprise the attaching member according to any of variations 1 to 3, an expandable portion is provided between the holding portion and the body, and the holding portion is displaceable relative to the body with expansion and contraction of the expandable portion.

Variation 7 may comprise the attaching member according to any of variations 1 to 3, the holding portion and the body are separate from each other, and the holding portion is displaceable by moving away from the body.

Variation 8 may comprise the attaching member according to any of variations 1 to 3, the body includes a plurality of separate components each provided with the holding portion, and the separate components are movable toward and away from one another.

Variation 9 may comprise the attaching member according to any of variations 1 to 3, the body includes a bellows area that is expandable and contractible, and the holding portion is displaceable with expansion and contraction of the bellows area.

Variation 10 may comprise the attaching member according to any of variations 1 to 3, the holding portion holds an inlet-side connector and an outlet-side connector of the pump tube and is configured such that the inlet-side connector is displaceable by a greater amount than the outlet-side connector.

Variation 11 may comprise in the attaching member according to any of variations 1 to 10, the body is provided with a tube forming a liquid flow route connected to a connector of the pump tube.

Variation 12 may comprise the attaching member according to any of variations 1 to 11, the blood purification apparatus includes a detecting unit that detects a state of the attaching member by coming into contact with a predetermined area inside the holding portion and applying an urging force to the predetermined area, and displacement of the holding portion caused by the urging force of the detecting unit is prevented.

Variation 13 may comprise a blood purification circuit connected to the pump tube according to any of variations 1 to 12 including a blood circuit through which blood is caused to extracorporeally circulate, and a flow route through which substitution fluid is introduced into the blood circuit or a flow route through which dialysate is introduced into a blood purifier connected to the blood circuit or through which drain liquid is drained from the blood purifier.

Variation 1 may comprise the attaching member includes the body attachable to the predetermined position of the blood purification apparatus, and the holding portion attached to the body and that holds the pump tube. The holding portion is displaceable relative to the body. Therefore, a load occurring on the pump tube that is being attached or detached can be released. Consequently, the work of attaching or detaching the pump tube to or from the peristaltic pump can be performed stably.

Variation 2 may comprise the holding portion includes the anchoring part at which the holding portion is anchorable by the anchor member included in the blood purification apparatus, and the pump tube is attachable to the peristaltic pump when the holding portion is anchored by the anchor member at the anchoring part. Therefore, the work of attaching the pump tube to the peristaltic pump can be automated easily.

Variation 3 may comprise the holding portion includes the anchoring part at which the holding portion is anchorable by the anchor member included in the blood purification apparatus, and the pump tube is detachable from the peristaltic pump by moving the anchor member when the anchor member is anchored to the holding portion at the anchoring part. Therefore, the work of detaching the pump tube from the peristaltic pump can be automated easily.

Variation 4 may comprise the holding portion is displaceable by rocking relative to the body. Therefore, a load occurring on the pump tube that is being attached or detached can be released with the rocking of the holding portion relative to the body.

Variation 5 may comprise the holding portion is continuous with and folded with respect to the body and is rockable about the folded area. That is, the attaching member can be obtained by forming the body and the holding portion continuously with each other and then folding the holding portion. Therefore, the attaching member can be manufactured easily. Variation 6 may comprise the expandable portion is provided between the holding portion and the body, and the holding portion is displaceable relative to the body with the expansion and contraction of the expandable portion. Therefore, the amount of displacement of the holding portion relative to the body can be set arbitrarily.

Variation 7 may comprise the holding portion and the body are separate from each other, and the holding portion is displaceable by moving away from the body. Therefore, a load occurring on the pump tube that is being attached or detached can be released with the movement of the holding portion away from the body.

Variation 8 may comprise the body includes the plurality of separate components each provided with the holding portion, and the separate components are movable toward and away from one another. Therefore, a load occurring on the pump tube that is being attached or detached can be released with the movements of the separate components toward and away from one another.

Variation 9 may comprise the body includes the bellows area that is expandable and contractible, and the holding portion is displaceable with the expansion and contraction of the bellows area. Therefore, a load occurring on the pump tube that is being attached or detached can be released with the expansion and contraction of the bellows area.

Variation 10 may comprise the holding portion holds the inlet-side connector and the outlet-side connector of the pump tube and is configured such that the inlet-side connector is displaceable by a greater amount than the outlet-side connector. Therefore, the work of detaching the pump tube from the peristaltic pump can be performed much more easily.

Variation 11 may comprise the body is provided with the tube forming the liquid flow route connected to the connector of the pump tube. Therefore, the tube connected to the pump tube can be handled easily.

Variation 12 may comprise the blood purification apparatus includes the detecting unit that detects the state of the attaching member by coming into contact with the predetermined area inside the holding portion and applying the urging force to the predetermined area, and the displacement of the holding portion caused by the urging force of the detecting unit is prevented. Therefore, a situation where the holding portion is accidentally displaced by the urging force of the detecting unit can be avoided.

Variation 13 may comprise a blood purification circuit that produces the advantageous effects according to any of variations 1 to 12 can be provided.

BRIEF DESCRIPTION OF THE DRAWINGS

FIG. 1 is an overall diagram of a blood purification apparatus, with an attaching member according to an embodiment of the present teachings attached thereto.

FIG. 2 is an overall diagram of the blood purification apparatus, with the attaching member yet to be attached thereto.

FIG. 3 is an enlargement of peristaltic pumps, with pump tubes of the attaching member yet to be attached thereto.

FIG. 4 is an enlargement of a part of the blood purification apparatus, with the attaching member anchored thereto.

FIG. 5 illustrates a process of attaching the pump tube to the peristaltic pump of the blood purification apparatus, including diagram (a) illustrating a state before an anchor member is moved, diagram (b) illustrating a state after the anchor member is moved but before loading is complete, and diagram (c) illustrating a state after loading is complete.

FIG. 6 illustrates a process of detaching the pump tube from the peristaltic pump of the blood purification apparatus, including diagram (a) illustrating a state before the anchor member is moved, diagram (b) illustrating a state after the anchor member is moved but before unloading is complete, and diagram (c) illustrating a state after unloading is complete.

FIG. 7 is a perspective view of an attaching member according to a first embodiment of the present teachings.

FIG. 8 is a front view of the attaching member.

FIG. 9 is a sectional view taken along line IX-IX illustrated in FIG. 8.

FIG. 10 is a sectional view taken along line X-X illustrated in FIG. 8.

FIG. 11 is a perspective view of the attaching member, with holding portions thereof holding pump tubes.

FIG. 12 is a front view of the attaching member holding the pump tubes.

FIG. 13 is a side view of the attaching member holding the pump tubes.

FIG. 14 is a third-angle projection of the attaching member, with the holding portions yet to be folded.

FIG. 15 includes diagrams of the attaching member and illustrate a state where the holding portion is anchored by the anchor member at an anchoring part thereof, and a state where the holding portion is pushed by the anchor member.

FIG. 16 is a diagram of the attaching member and illustrates a state where the holding portion is rocked relative to a body.

FIG. 17 is a diagram illustrating a blood purification apparatus with the attaching member attached thereto, and is provided for describing blood purification treatment.

FIG. 18 is a diagram illustrating a state of the attaching member attached to the blood purification apparatus, with a detecting unit being in contact with a predetermined area inside the holding portion (a state before the setting of the attaching member is complete).

FIG. 19 is a diagram illustrating another state of the attaching member attached to the blood purification apparatus, with the detecting unit being in contact with the predetermined area inside the holding portion (a state after the setting of the attaching member is complete).

FIG. 20 includes diagrams of an attaching member according to another embodiment of the present teachings that includes an expandable portion (a pantograph portion) provided between a holding portion and a body.

FIG. 21 includes diagrams of an attaching member according to yet another embodiment of the present teachings that includes an expandable portion (a bellows portion) provided between a holding portion and a body.

FIG. 22 is a perspective view of an attaching member according to a second embodiment of the present teachings (with holding portions being spaced apart from a body).

FIG. 23 is a second-angle projection of the attaching member (with the holding portions yet to be spaced apart from the body).

FIG. 24 is a front perspective view of an attaching member according to a third embodiment of the present teachings (with holding portions being in proximity to a body).

FIG. 25 is a rear perspective view of the attaching member (with the holding portions being in proximity to the body).

FIG. 26 is a front perspective view of the attaching member (with the holding portions being spaced apart from the body).

FIG. 27 is a rear perspective view of the attaching member (with the holding portions being spaced apart from the body).

FIG. 28 is a perspective view of an attaching member according to a fourth embodiment of the present teachings (that includes a bellows area).

FIG. 29 is a perspective view of an attaching member according to a fifth embodiment of the present teachings (in which inlet-side connectors are displaceable by a greater amount than outlet-side connectors).

FIG. 30 is a side view of the attaching member, with a holding portion being displaced.

DETAILED DESCRIPTION

Embodiments of the present teachings will now be described specifically with reference to the drawings.

An attaching member according to a first embodiment is to be attached to a blood purification apparatus including peristaltic pumps. The attaching member holds pump tubes to be squeezed in a predetermined direction by the peristaltic pumps for liquid delivery. As illustrated in FIGS. 1 to 13, the attaching member includes a body 2 attachable to a predetermined position of a blood purification apparatus B, and holding portions 3 attached to the body 2 and that hold pump tubes C.

As illustrated in FIG. 14, the attaching member 1 is a resin molded component in which the body 2 and the holding portions 3 are formed continuously with each other. When the component is folded at folds K extending along the boundaries between the body 2 and the holding portions 3, the holding portions 3 are placed on the front face of the body 2 as illustrated in FIG. 7. The folds K each have perforations or the like. Therefore, the holding portions 3 are easily foldable with respect to the body 2.

As illustrated in FIGS. 7 to 13, the body 2 according to the present embodiment is a rectangular resin molded part and has inclined surfaces 2a provided on two opposite sides thereof, respectively. The inclined surfaces 2a are each inclined at a predetermined angle with respect to the bottom surface of the body 2 (an attaching surface that faces a predetermined position Ba). Furthermore, the body 2 includes a central portion 2b positioned in the center of the body 2 and between the left and right inclined surfaces 2a. Specifically, the body 2 has the central portion 2b in the center thereof, with the inclined surfaces 2a inclined at the angle α extending from the central portion 2b toward the left and right sides, respectively. The inclined surfaces 2a carry a plurality of (four in the present embodiment) holding portions 3.

The holding portions 3 are each a resin molded part projecting in a block-like shape from the body 2 (projecting frontward). The holding portions 3 have holding grooves 3a (see FIGS. 7 to 10), into each of which one of connectors D provided at two respective ends of each of the pump tubes C is to be fitted, whereby the connectors D are securable at a predetermined height. In short, the connectors D are secured by being fitted into the holding grooves 3a, whereby the pump tubes C are held by the holding portions 3 as illustrated in FIGS. 11 to 13. Furthermore, as illustrated in FIG. 9, the holding portions 3 have anchoring holes 3b (anchoring parts) in predetermined areas thereof and are therefore anchorable by anchor members A included in the blood purification apparatus B.

The pump tubes C are each made of a material such as soft resin or rubber forming a flow route with a relatively large diameter. Each pump tube C has the connectors D at one end and the other end thereof, respectively. After the pump tube C is fitted into a stator S of a corresponding one of the peristaltic pumps P, a rotor R is driven to rotate. Thus, the pump tube C is squeezed in the lengthwise direction by rollers Ra, so that liquid such as substitution fluid or drain liquid can be delivered.

As illustrated in FIGS. 9, 10, and 13, the holding portions 3 according to the present embodiment are provided on the inclined surfaces 2a. Therefore, the pump tubes C each extend at a predetermined angle α (inclined along the inclined surface 2a) with respect to the bottom surface of the body 2 (the attaching surface that faces the predetermined position Ba). In other words, the holding portions 3 according to the present embodiment hold the connectors D of the pump tubes C in an inclined state. Specifically, the holding portions 3 hold the pump tubes C such that the pump tubes C are inclined in a direction in which the pump tubes C are fitted to the peristaltic pumps P (a downward direction in FIG. 13).

The body 2 according to the present embodiment is configured such that tubes (not illustrated) forming liquid flow routes connected to the connectors D of the pump tubes C are placed in the central portion 2b thereof. Specifically, the central portion 2b of the body 2 according to the present embodiment has a concavity that is open on the rear side, and the tubes (not illustrated) connected to the connectors D of the pump tubes C are placed along the concavity.

As illustrated in FIGS. 1 to 3, the blood purification apparatus B applied to the present embodiment is a monitoring apparatus for hemodialysis treatment that includes a monitor M capable of displaying information regarding blood purification treatment and the like, a blood pump N, and so forth. When the blood pump N is activated, blood of a patient is caused to extracorporeally circulate through a blood circuit. Meanwhile, the blood undergoes blood purification treatment in a blood purifier (a dialyzer). The blood purification apparatus B according to the present embodiment includes a plurality of (seven in the present embodiment) peristaltic pumps P provided on the front face thereof, so that substitution fluid and drain liquid can be delivered in the blood purification treatment.

The peristaltic pumps P are each capable of delivering liquid by squeezing the pump tube C in a specific direction and each include, as illustrated in FIGS. 3 to 6, the stator S having a fitting recess Sa, the rotor R provided in the fitting recess Sa and being rotatable about a rotating shaft L, and the rollers Ra provided on the rotor R. When the pump tube C is fitted into the fitting recess Sa of the stator S and the rotor R is driven to rotate, the pump tube C is squeezed between the wall of the fitting recess Sa and the rollers Ra. Thus, the liquid can be delivered.

The rotor R has an upper guide pin a1 and a lower guide pin a2 provided in a pair, and an upper guide pin b1 and a lower guide pin b2 provided in a pair, all of which project from the rotor R. The pump tube C is to be fitted between the upper guide pin a1 and the lower guide pin a2 and between the upper guide pin b1 and the lower guide pin b2. The upper guide pins a1 and b1 are positioned on the open side of the fitting recess Sa. The lower guide pins a2 and b2 are positioned on the bottom side of the fitting recess Sa. Thus, the pump tube C fitted in the fitting recess Sa is prevented from being displaced from a predetermined position (a position where the pump tube C is squeezable by the rollers Ra).

The blood purification apparatus B according to the present embodiment receives the attaching member 1 attachable to the predetermined position Ba on the front face thereof, where the peristaltic pumps P are provided. Specifically, as illustrated in FIG. 4, the blood purification apparatus B according to the present embodiment has a positioning pin g. When the positioning pin g is inserted into a positioning hole h provided in the body 2 of the attaching member 1, the attaching member 1 can be positioned at the predetermined position Ba of the blood purification apparatus B.

As illustrated in FIG. 2, the blood purification apparatus B according to the present embodiment further has a plurality of anchor members A at the predetermined position Ba. Meanwhile, as described above, the holding portions 3 have the anchoring holes 3b (the anchoring parts) at which the holding portions 3 are anchorable by the anchor members A. As illustrated in FIGS. 15 and 16, the anchor members A each include an anchor hook Aa on one side of the distal end thereof, and a pushing portion Ab on the other side. The anchor hook Aa is hooked on the peripheral edge of the anchoring hole 3b (see FIG. 15(a)). Thus, the attaching member 1 is anchored by the anchor member A and is secured to the predetermined position Ba.

In a state where the attaching member 1 is positioned by the positioning pin g and is anchored at the anchoring holes 3b (the anchoring parts) by the anchor hooks Aa of the anchor members A (see FIG. 15(a)), as illustrated in FIG. 5(a), proximal portions Ca and a distal portion Cb of each of the pump tubes C held by the holding portions 3 are positioned above the upper guide pins a1 and b1 of a corresponding one of the peristaltic pumps P. Meanwhile, the rotor R of each of the peristaltic pumps P is stopped at a predetermined position (see FIGS. 2 to 4). In such an anchoring state, the anchor member A is moved in such a direction as to sink into the predetermined position Ba (a direction in which the attaching member 1 is moved toward the predetermined position Ba). Then, as illustrated in FIG. 5(b), the proximal portions Ca of the pump tube C are positioned between the upper guide pin b1 and the lower guide pin b2, while the distal portion Cb of the pump tube C is positioned above the upper guide pin a1.

In such a state, the rotor R is driven to rotate. Then, as illustrated in FIG. 5(c), while the proximal portions Ca of the pump tube C are positioned between the upper guide pin a1 and the lower guide pin a2, the distal portion Cb of the pump tube C interferes with the upper guide pin b1 and is drawn to a position between the upper guide pin b1 and the lower guide pin b2. Thus, the pump tube C is set in the peristaltic pump P. Such attaching work of setting the pump tube C by drawing the pump tube C to the position between the upper guide pin a1 and the lower guide pin a2 is also referred to as loading.

On the other hand, in the state where the pump tube C is set in the peristaltic pump P as illustrated in FIG. 6(a) with the anchor member A anchoring at the anchoring hole 3b (the anchoring part), the anchor member A is moved in a direction of projection thereof (a direction in which the attaching member 1 is lifted from the predetermined position Ba). Then, the pushing portion Ab of the anchor member A pushes the peripheral edge of the anchoring hole 3b (see FIG. 15(b)) and lifts the pump tube C from the fitting recess Sa. Meanwhile, the rotor R of each of the peristaltic pumps P is stopped at the same predetermined position (see FIGS. 2 to 4) as in the case of the loading of the pump tube. Furthermore, as illustrated in FIG. 6(b), the distal portion Cb of the pump tube C is positioned between the upper guide pin a1 and the lower guide pin a2, while the proximal portions Ca of the pump tube C are positioned above the upper guide pin b1.

In such a state, the rotor R is driven to rotate. Then, as illustrated in FIG. 6(c), while the proximal portions Ca of the pump tube C are positioned above the upper guide pin a1, the distal portion Cb of the pump tube C interferes with the upper guide pin b1 and is pushed to a position above the upper guide pin b1. Thus, the pump tube C that has been set in the peristaltic pump P is unset and is allowed to be detached. Such detaching work of unsetting the pump tube C by pushing out the pump tube C from the position between the upper guide pin a1 and the lower guide pin a2 is also referred to as unloading.

The holding portions 3 of the attaching member 1 according to the present embodiment are displaceable relative to the body 2. If a load occurs on any of the pump tubes C that are being attached to or detached from the peristaltic pumps P, a corresponding one of the holding portions 3 rocks in such a direction as to release the load. Thus, the holding portion 3 is displaceable relative to the body 2. Specifically, the holding portions 3 are each rockable about the fold K relative to the body 2. If a load occurs on any of the pump tubes C, the corresponding holding portion 3 rocks in such a direction as to be pulled toward the body 2, whereby the load is released.

For example, if a load occurs on any of the pump tubes C in the process of loading the pump tubes C onto the peristaltic pumps P in fitting the pump tubes C to the peristaltic pumps P, a corresponding one of the holding portions 3 rocks about the fold K as illustrated in FIG. 16.

Thus, the load can be released. Even if a load occurs with the interference between the anchor member A and the peripheral edge of the anchoring hole 3b in the process of inserting the anchor member A into the anchoring hole 3b of the holding portion 3, the holding portion 3 rocks about the fold K as illustrated in the drawing. Thus, the load can be released.

On the other hand, if a load occurs on any of the pump tubes C in the process of unloading the pump tubes C from the peristaltic pumps P in removing the pump tubes C from the peristaltic pumps P, a corresponding one of the holding portions 3 rocks about the fold K as illustrated in FIG. 16. Thus, the load can be released. Even if a load occurs with the interference between the pump tube C and the rotor R or the like of the peristaltic pump P during the blood purification treatment, the holding portion 3 rocks about the fold K as illustrated in the drawing. Thus, the load can be released.

When the attaching member 1 is anchored to the predetermined position of the blood purification apparatus B and the pump tubes C are loaded onto the respective peristaltic pumps P, a treatment apparatus for blood purification treatment is established as illustrated in FIG. 17. The treatment apparatus includes a blood circuit U including a dialyzer Q; a first dialysate introduction line L1a and a second dialysate introduction line L1b through which dialysate is introduced into the dialyzer Q; a first substitution line L2a, a second substitution line L2b, a pre-substitution line L2c, and a post-substitution line L2d through which substitution fluid is supplied to the blood circuit U; and a first drain-liquid discharge line L3a and a second drain-liquid discharge line L3b through which drain liquid is drained from the dialyzer Q.

The blood circuit U includes an arterial blood circuit Ua and a venous blood circuit Ub. When the blood pump N is activated while a patient is punctured with the distal ends of the arterial blood circuit Ua and the venous blood circuit Ub, blood of the patient can be caused to extracorporeally circulate. The dialyzer Q has a blood introduction port Qa, a blood delivery port Qb, a dialysate introduction port Qc, and a dialysate delivery port Qd all projecting from a housing thereof. The arterial blood circuit Ua is connected to the blood introduction port Qa. The venous blood circuit Ub is connected to the blood delivery port Qb. The second dialysate introduction line L1b is connected to the dialysate introduction port Qc. The first drain-liquid discharge line L3a is connected to the dialysate delivery port Qd.

The first dialysate introduction line L1a is connected to a dialysate bag W1 that stores dialysate and is also connected to the second dialysate introduction line L1b through a temporary chamber T. When the peristaltic pumps P provided to the first dialysate introduction line L1a and the second dialysate introduction line L1b are activated, the dialysate in the dialysate bag W1 is temporarily stored in the temporary chamber T and is then introduced into the dialyzer Q.

The first substitution L2a is connected to a substitution-fluid bag W2 that stores substitution fluid and is also connected to the second substitution line L2b through a temporary chamber T. The second substitution line L2b is connected to the blood circuit U through the pre-substitution line L2c connected to the arterial blood circuit Ua and through the post-substitution line L2d connected to the venous blood circuit Ub. The post-substitution line L2d is provided with a check valve V1. When the peristaltic pumps P provided to the first substitution line L2a and the second substitution line L2b are activated, the substitution fluid in the substitution-fluid bag W2 is temporarily stored in the temporary chamber T and is then introduced into the arterial blood circuit Ua or the venous blood circuit Ub in accordance with the state of operation of the peristaltic pump P provided to the pre-substitution line L2c.

The first drain-liquid discharge line L3a is connected to the dialyzer Q and is also connected to the second drain-liquid discharge line L3b through a temporary chamber T. The second drain-liquid discharge line L3b allows the drain liquid to be drained therethrough to the outside of the apparatus. When the peristaltic pumps P provided to the first drain-liquid discharge line L3a and the second drain-liquid discharge line L3b are activated, the drain liquid in the dialyzer Q is temporarily stored in the temporary chamber T and is then allowed to be drained to the outside of the apparatus.

As described above, the pump tubes C of the attaching member 1 are connected to the flow routes (the first substitution line L2a, the second substitution line L2b, and the pre-substitution line L2c) for introducing the substitution fluid into the blood circuit U, the flow routes (the first dialysate introduction line L1a and the second dialysate introduction line L1b) for introducing the dialysate into the dialyzer Q (a blood purifier) connected to the blood circuit U, and the flow routes (the first drain-liquid discharge line L3a and the second drain-liquid discharge line L3b) for draining the drain liquid from the dialyzer Q (the blood purifier). The post-substitution line L2d may also be connected to one of the pump tubes C of the attaching member 1.

In the present embodiment, none of the pump tubes C of the attaching member 1 is attached to the blood pump N. Alternatively, one of the pump tubes C of the attaching member 1 may be attached to the blood pump N by loading the pump tube C thereon. In such a case, what is to be connected to the pump tube C of the attaching member 1 is the blood circuit U. That is, devices that are loadable onto the pump tubes C of the attaching member 1 according to the present teachings include a blood purification circuit that includes the following: the blood circuit U for causing the blood to extracorporeally circulate, the flow routes (the first dialysate introduction line L1a and the second dialysate introduction line L1b) for introducing the substitution fluid into the blood circuit U, the flow routes (the first substitution line L2a, the second substitution line L2b, and the pre-substitution line L2c (or the post-substitution line L2d)) for introducing the dialysate into the dialyzer Q (the blood purifier) connected to the blood circuit U, or the flow routes (the first drain-liquid discharge line L3a and the second drain-liquid discharge line L3b) for draining the drain liquid from the dialyzer Q (the blood purifier).

The blood purification apparatus B according to the present embodiment further includes detecting units H that each detect a situation where a corresponding one of the pump tubes C has fallen into an attachable state or a detachable state. As illustrated in FIGS. 18 and 19, the detecting units H each include a bar-like member Ha that is allowed to come into contact with a predetermined area defined inside a corresponding one of the holding portions 3 of the attaching member 1 attached to the predetermined position Ba. The bar-like member Ha is urged by a spring Hb in such a direction as to project. When the attaching member 1 is displaced from an unset position (see FIG. 18) to a set position (see FIG. 19), the bar-like member Ha of the detecting unit H follows the movement of the attaching member 1 and thus moves against the urging force exerted by the spring Hb. The spring Hb is incorporated such that one end thereof is in contact with a supporting frame f1 fixed to the blood purification apparatus B, and the other end thereof is in contact with the bar-like member Ha.

The bar-like member Ha of the detecting unit H is provided with a stopper Jb at the proximal end thereof. A resistor Ja is fixed to a supporting frame f2 at a position near the proximal end of the bar-like member Ha. The resistor Ja and the stopper Jb form a potentiometer J. When the bar-like member Ha of the detecting unit H is moved to move the stopper Jb, the resistor Ja converts the movement into a voltage corresponding to the length of travel and the position of the stopper Jb (i.e., the length of travel and the position of the bar-like member Ha of the detecting unit H). Thus, the potentiometer J can output the voltage.

Hence, in a case where the attaching member 1 is to be moved from the unset position (see FIG. 18) to the set position (see FIG. 19), if, for example, any pump tube C interferes with any elements of the peristaltic pump P and so forth and fails to be in the set position, i.e., the attachable state, a situation where the length of travel of the bar-like member Ha is different from a normal length of travel can be detected from the voltage outputted by the potentiometer J. Furthermore, in the present embodiment, if any pump tube C that has failed to be in the attachable state is detected by the detecting unit H, a corresponding one of the peristaltic pumps P can be identified.

Likewise, in a case where the attaching member 1 is to be moved from the set position (see FIG. 19) to the unset position (see FIG. 18), if, for example, any pump tube C interferes with any elements of the peristaltic pump P and so forth and fails to be in the unset position, i.e., the detachable state, a situation where the length of travel of the bar-like member Ha is different from the normal length of travel can be detected from the voltage outputted by the potentiometer J. Furthermore, in the present embodiment, if any pump tube C that has failed to be in the detachable state is detected by the detecting unit H, a corresponding one of the peristaltic pumps P can be identified.

The attaching member 1 may be configured such that displacement of the holding portion 3 caused by the urging force of the detecting unit H (specifically, the urging force exerted by the spring Hb) is prevented. In such a configuration, as illustrated in FIGS. 18 and 19, the distal end of the bar-like member Ha (the detecting unit H) may come into contact with both a top inner surface t1 and a peripheral inner surface t2 of the holding portion 3 (for example, a corner part may be defined between the top inner surface t1 and the peripheral inner surface t2 on a side of the holding portion 3 that is nearer to the center of the attaching member 1 (a side adjoining the peripheral inner surface t2)). Thus, a situation where the holding portion 3 is accidentally displaced by the urging force of the detecting unit H can be avoided. Consequently, accidental failure in the anchoring by the anchor member A can be prevented.

Alternatively to the above embodiment, the following may be employed: an embodiment in which the displacement of the holding portion 3 caused by the urging force of the detecting unit H is prevented by bringing an outer peripheral surface t3 (a surface that faces the stator S) of the holding portion 3 into contact with the stator S of the peristaltic pump P (for example, an embodiment in which the stator S has a projection that comes into contact with the outer peripheral surface t3, an embodiment in which the outer peripheral surface t3 of the holding portion 3 has a projection that comes into contact with the stator S, or an embodiment in which a spacer is provided between the stator S and the outer peripheral surface t3), an embodiment in which an area inside the holding portion 3 with which the bar-like member Ha comes into contact has a concavity to prevent the displacement of the holding portion 3 caused by the urging force of the detecting unit H, or the like.

According to the above embodiment, the attaching member 1 includes the body 2 attachable to the predetermined position Ba of the blood purification apparatus B, and the holding portions 3 attached to the body 2 and that holds the pump tubes C. The holding portions 3 are each displaceable relative to the body 2. Therefore, a load occurring on any of the pump tubes C that are being attached or detached can be released. Consequently, the work of attaching (loading) or detaching (unloading) the pump tubes C to or from the peristaltic pumps P can be performed stably. In particular, the body 2 according to the present embodiment is provided with the tubes (not illustrated) forming the liquid flow routes connected to the connectors D of the pump tubes C. Therefore, the tubes (not illustrated) connected to the pump tubes C can be handled easily.

The holding portions 3 according to the present embodiment have the anchoring holes 3b (the anchoring parts) at which the holding portions 3 are anchorable by the anchor members A included in the blood purification apparatus B. The pump tubes C are attachable to the peristaltic pumps P when the holding portions 3 are anchored by the anchor members A at the anchoring holes 3b (the anchoring parts). Therefore, the work of attaching the pump tubes C to the peristaltic pumps P can be automated easily. Likewise, the holding portions 3 according to the present embodiment have the anchoring holes 3b (the anchoring parts) at which the holding portions 3 are anchorable by the anchor members A included in the blood purification apparatus B. The pump tubes C are detachable from the peristaltic pumps P by moving the anchor members A when the anchor members A are anchored to the holding portions 3 at the anchoring holes 3b (the anchoring parts). Therefore, the work of detaching the pump tubes C from the peristaltic pumps P can be automated easily.

The holding portions 3 according to the present embodiment are each displaceable by rocking relative to the body 2. Therefore, a load occurring on any of the pump tubes C that are being attached or detached can be released with the rocking of the holding portions 3 relative to the body 2. The holding portions 3 according to the present embodiment are each continuous with and folded with respect to the body 2 and are each rockable about the fold K. That is, the attaching member 1 can be obtained by forming the body 2 and the holding portions 3 continuously with each other and then folding the holding portions 3. Therefore, the attaching member 1 can be manufactured easily.

The holding portions 3 according to the above embodiment are each displaceable by rocking relative to the body 2. Alternatively, an expandable portion may be provided between the holding portions 3 and the body 2, and the holding portions 3 may each be displaceable relative to the body 2 with the expansion and contraction of the expandable portion. For example, the following may be employed: an embodiment illustrated in FIG. 20 in which a pantograph portion 4 as the expandable portion is provided between the holding portions 3 and the body 2 so that the holding portions 3 are displaceable relative to the body 2 with the expansion and contraction of the pantograph portion 4, or an embodiment illustrated in FIG. 21 in which a bellows portion 5 as the expandable portion is provided between the holding portions 3 and the body 2 so that the holding portions 3 are displaceable relative to the body 2 with the expansion and contraction of the bellows portion 5.

Since the expandable portion in the form of the pantograph portion 4 or the bellows portion 5 is provided between the holding portions 3 and the body 2 so that the holding portions 3 are displaceable relative to the body 2 with the expansion and contraction of the expandable portion, the amount of displacement of the holding portions 3 relative to the body 2 can be set arbitrarily. The expandable portion is not limited to the pantograph portion 4 or the bellows portion 5 and only needs to be an element that is capable of absorbing the load by displacing the holding portions 3 relative to the body 2 with the expansion and contraction thereof.

Now, an attaching member according to a second embodiment of the present teachings will be described.

As with the case of the first embodiment, an attaching member 1 according to the present embodiment is to be attached to a blood purification apparatus including peristaltic pumps. The attaching member 1 holds pump tubes to be squeezed in a predetermined direction by the peristaltic pumps for liquid delivery. As illustrated in FIGS. 22 and 23, the attaching member 1 includes a body 2 attachable to a predetermined position of a blood purification apparatus B, and holding portions 3 attached to the body 2 and that hold pump tubes C. The blood purification apparatus B applicable herein has the same configuration as that of the first embodiment, and detailed description thereof is omitted.

The holding portions 3 and the body 2 according to the present embodiment are separate from each other. The holding portions 3 are displaceable by moving away from the body 2. As illustrated in FIG. 22, the body 2 according to the present embodiment has anchor portions f capable of anchoring the holding portions 3. The holding portions 3 are anchored to the anchor portions f, whereby the holding portions 3 are attached to the body 2 to form a unit. If a load occurs on any of the pump tubes C that are being attached to or detached from the peristaltic pumps P, the anchoring by the anchor portions f is undone to separate the holding portions 3 from the body 2. Thus, the load can be released.

According to the present embodiment, the holding portions 3 and the body 2 are separate from each other, and the holding portions 3 are displaceable by moving away from the body 2. Therefore, a load occurring on any of the pump tubes C that are being attached or detached can be released with the movement of the holding portions 3 away from the body 2. If the force of anchoring the holding portions 3 by the anchor portions f is adjusted arbitrarily, the degree of the releasable load can be adjusted.

Now, an attaching member according to a third embodiment of the present teachings will be described.

As with the case of the first embodiment, an attaching member 1 according to the present embodiment is to be attached to a blood purification apparatus including peristaltic pumps. The attaching member 1 holds pump tubes to be squeezed in a predetermined direction by the peristaltic pumps for liquid delivery. As illustrated in FIGS. 24 to 27, the attaching member 1 includes a body 6 attachable to a predetermined position of a blood purification apparatus B, and holding portions 3 attached to the body 6 and that hold pump tubes C. The blood purification apparatus B applicable herein has the same configuration as that of the first embodiment, and detailed description thereof is omitted.

The body 6 according to the present embodiment includes a plurality of separate components (in the present embodiment, a first body 6a and a second body 6b) each provided with holding portions 3. The load applied to the pump tubes C is releasable with the movements of the separate components toward and away from each other. Specifically, the first body 6a and the second body 6b are coupled to each other by coupling portions 6c in such a manner as to be independently slidable relative to each other. The attaching member 1 is attached to the predetermined position Ba of the blood purification apparatus B, with the first body 6a and the second body 6b being in proximity to each other (see FIGS. 24 and 25). If a load occurs on any of the pump tubes C, the first body 6a and the second body 6b move from each other (see FIGS. 26 and 27). Thus, the load can be released.

According to the present embodiment, the body 6 includes a plurality of separate components (the first body 6a and the second body 6b) each provided with the holding portions 3, and the separate components are movable toward and away from each other. Therefore, a load occurring on any of the pump tubes C that are being attached or detached can be released with the movements of the separate components toward and away from each other. The holding portions 3 may be three or more components that are separate from one another and movable toward and away from one another. The plurality of separate components may be coupled to one another in another way.

Now, an attaching member according to a fourth embodiment of the present teachings will be described.

As with the case of the first embodiment, an attaching member 1 according to the present embodiment is to be attached to a blood purification apparatus including peristaltic pumps. The attaching member 1 holds pump tubes to be squeezed in a predetermined direction by the peristaltic pumps for liquid delivery. As illustrated in FIG. 28, the attaching member 1 includes a body 7 attachable to a predetermined position of a blood purification apparatus B, and holding portions 3 attached to the body 7 and that hold pump tubes C. The blood purification apparatus B applicable herein has the same configuration as that of the first embodiment, and detailed description thereof is omitted.

The body 7 according to the present embodiment includes in a central portion thereof a bellows portion 7a that is expandable and contractible. The holding portions 3 are displaceable with the expansion and contraction of the bellows portion 7a. The load applied to the pump tubes C is releasable with the expansion and contraction of the bellows portion 7a. Specifically, the body 7 includes the bellows portion 7a provided between one side region having the holding portions 3 and the other side region having the holding portions 3. The body 7 is to be attached to the predetermined position Ba of the blood purification apparatus B. If a load occurs on any of the pump tubes C, the bellows portion 7a expands to release the load.

According to the present embodiment, the body 7 includes the bellows portion 7a that is expandable and contractible, and the holding portions 3 are displaceable with the expansion and contraction of the bellows portion 7a. Therefore, a load occurring on any of the pump tubes C that are being attached or detached can be released with the expansion and contraction of the bellows portion 7a. The bellows portion 7a is formed as a part of the body 7. Alternatively, a separately prepared bellows portion 7a that is expandable and contractible may be attached to a central portion of the body 7.

Now, an attaching member according to a fifth embodiment of the present teachings will be described.

As with the case of the first embodiment, an attaching member 1 according to the present embodiment is to be attached to a blood purification apparatus including peristaltic pumps. The attaching member 1 holds pump tubes to be squeezed in a predetermined direction by the peristaltic pumps for liquid delivery. As illustrated in FIGS. 29 and 30, the attaching member 1 includes a body 2 attachable to a predetermined position of a blood purification apparatus B, and holding portions 3 attached to the body 2 and that hold pump tubes C. The blood purification apparatus applicable herein has the same configuration as that of the first embodiment, and detailed description thereof is omitted.

The holding portions 3 according to the present embodiment hold inlet-side connectors D and outlet-side connectors D of the pump tubes C and are configured such that the inlet-side connectors D are displaceable by a greater amount than the outlet-side connectors D. Specifically, the holding portions 3 are each foldable along the fold K extending in the widthwise direction of the body 2. When any of the pump tubes C is unloaded from a corresponding one of the peristaltic pumps P, as illustrated in FIG. 30, a side of the holding portion 3 to which the inlet-side connector D is secured is pushed by a working member F provided on the blood purification apparatus B. Thus, the inlet-side connector D can be displaced by a greater amount than the outlet-side connector D. If a load occurs on any of the pump tubes C, a corresponding one of the holding portions 3 rocks about the fold K. Thus, the load can be released.

According to the present embodiment, the holding portions 3 hold the inlet-side connectors D and the outlet-side connectors D of the pump tubes C and are configured such that the inlet-side connectors D are displaceable by a greater amount than the outlet-side connectors D. Therefore, the work of detaching the pump tubes C from the peristaltic pumps P can be performed much more easily. In the present embodiment, the holding portions 3 are continuous with the body 2 and are folded at the fold K. Alternatively, the body 2 and the holding portions 3 may be separate from each other while being rockably coupled to each other such that the inlet-side connectors D are displaceable by a greater amount than the outlet-side connectors D.

While some embodiments have been described above, the present teachings are not limited thereto. For example, a plurality of, but not seven, peristaltic pumps P or a single peristaltic pump P may be provided on the blood purification apparatus B, and a number of pump tubes C that corresponds to the number of peristaltic pumps P may be held by the holding portions 3. The attaching member 1 according to each of the embodiments is anchored by the anchor members A included in the blood purification apparatus B and is configured such that the pump tubes C are unloaded from the peristaltic pumps P by moving the anchor members A in the direction of projection thereof. Alternatively, the anchor members A may be moved by actuators, by hand, or by any other means. The positions of the positioning pin g and the positioning hole h may be defined arbitrarily. Moreover, the present teachings may be applied to a blood purification apparatus B including no positioning pin g, with the attaching member 1 having no positioning hole h.

The attaching member may have other additional functions or the like, as long as the attaching member includes a body attachable to a predetermined position of a blood purification apparatus, and a holding portion attached to the body and that holds a pump tube, the holding portion being displaceable relative to the body.

REFERENCE SIGN LIST 1 attaching member
2 body
2a inclined surface
2b central portion
3 holding portion
3a holding groove
3b anchoring hole (anchoring part)
4 pantograph portion (expandable portion)
5 bellows portion (expandable portion)
6 body
6a first body
6b second body
6c coupling portion
7 body
7a bellows portion
K fold (rocking axis)
A anchor member
Aa anchor hook
Ab pushing portion
B blood purification apparatus (monitoring apparatus)
Ba predetermined position
C pump tube
D connector
M monitor
P peristaltic pump
S stator
Sa fitting recess
R rotor
Ra roller
a1, b1 upper guide pin
a2, b2 lower guide pin
L rotating shaft
g positioning pin
h positioning hole

The invention claimed is:

1. An attaching member to be attached to a blood purification apparatus including a peristaltic pump, the attaching member holding a pump tube to be squeezed in a predetermined direction by the peristaltic pump for liquid delivery, the attaching member comprising:
   a body attachable to a predetermined position of the blood purification apparatus; and
   a holding portion attached to the body and that holds the pump tube,
   wherein the holding portion is continuous with and folded with respect to the body and is displaceable by rocking, relative to the body, and the holding portion is displaceable about a folded area while holding the pump tube when the pump tube is being attached to or detached from the peristaltic pump.

2. The attaching member according to claim 1, wherein the holding portion includes an anchoring part at which the holding portion is anchorable by an anchor member included in the blood purification apparatus, and the pump tube is attachable to the peristaltic pump when the holding portion is anchored by the anchor member at the anchoring part.

3. The attaching member according to claim 1, wherein the holding portion includes an anchoring part at which the holding portion is anchorable by an anchor member included in the blood purification apparatus, and the pump tube is detachable from the peristaltic pump by moving the anchor member when the anchor member is anchored to the holding portion at the anchoring part.

4. The attaching member according to claim 1, wherein an expandable portion is provided between the holding portion and the body, and the holding portion is displaceable relative to the body with expansion and contraction of the expandable portion.

5. The attaching member according to claim 1, wherein the holding portion and the body are separate from each other, and the holding portion is displaceable by moving away from the body.

6. The attaching member according to claim 1, wherein the body includes a plurality of separate components each provided with the holding portion, and the separate components are movable toward and away from one another.

7. The attaching member according to claim 1, wherein the body includes a bellows area that is expandable and contractible, and the holding portion is displaceable with expansion and contraction of the bellows area.

8. The attaching member according to claim 1, wherein the holding portion holds an inlet-side connector and an outlet-side connector of the pump tube and is configured such that the inlet-side connector is displaceable by a greater amount than the outlet-side connector.

9. The attaching member according to claim 1, wherein the body is provided with a tube forming a liquid flow route connected to a connector of the pump tube.

10. The attaching member according to claim 1, wherein the blood purification apparatus includes a detecting unit that detects a state of the attaching member by coming into contact with a predetermined area inside the holding portion and applying an urging force to the predetermined area, and displacement of the holding portion caused by the urging force of the detecting unit is prevented.

11. A blood purification circuit to be connected to the pump tube according to claim 1 including a blood circuit through which blood is caused to extracorporeally circulate, and a flow route through which substitution fluid is introduced into the blood circuit or a flow route through which dialysate is introduced into a blood purifier connected to the blood circuit or through which drain liquid is drained from the blood purifier.

12. The attaching member according to claim 1, wherein the holding portion releases a load occurring on the pump tubes by the rocking of the holding portion in a direction relative to the body.

13. The attaching member according to claim 1, wherein the holding portion rocks in a direction as to be pulled toward the body.

14. The attaching member according to claim 1, wherein the holding portion is provided at a predetermined angle with respect to the body and the predetermined angle of the holding portion with respect to the body changes as the holding portion rocks relative to the body.

* * * * *